(12) United States Patent
Deperthes et al.

(10) Patent No.: US 8,975,370 B2
(45) Date of Patent: Mar. 10, 2015

(54) INHIBITOR PROTEINS OF A PROTEASE AND USE THEREOF

(75) Inventors: David Deperthes, Etoy (CH); Sylvain Cloutier, Quebec (CA)

(73) Assignee: Universite de Lausanne, Lausanne (CH)

( * ) Notice: Subject to any disclaimer, the term of this patent is extended or adjusted under 35 U.S.C. 154(b) by 1133 days.

(21) Appl. No.: 10/552,786

(22) PCT Filed: Apr. 5, 2004

(86) PCT No.: PCT/IB2004/001040

§ 371 (c)(1),
(2), (4) Date: Jul. 25, 2006

(87) PCT Pub. No.: WO2004/087912

PCT Pub. Date: Oct. 14, 2004

(65) Prior Publication Data

US 2006/0269536 A1 Nov. 30, 2006

Related U.S. Application Data

(60) Provisional application No. 60/460,345, filed on Apr. 4, 2003.

(51) Int. Cl.

| *A61K 38/04* | (2006.01) |
| *A61K 38/00* | (2006.01) |
| *A23J 1/00* | (2006.01) |
| *C12P 21/06* | (2006.01) |
| *C12P 21/04* | (2006.01) |
| *C12N 15/62* | (2006.01) |
| *C07K 14/81* | (2006.01) |

(52) U.S. Cl.
CPC ............ *C12N 15/62* (2013.01); *C07K 14/8121* (2013.01); *A61K 38/00* (2013.01); *C07K 2319/21* (2013.01); *C07K 2319/50* (2013.01)
USPC ........... 530/327; 530/300; 530/333; 530/413; 435/69.1; 435/71.2

(58) Field of Classification Search
None
See application file for complete search history.

(56) References Cited

U.S. PATENT DOCUMENTS 5,827,662 A   10/1998   Rubin et al.

FOREIGN PATENT DOCUMENTS

| EP | 1029921 A1 | 8/2000 |
| WO | WO-95/27053 A1 | 10/1995 |

OTHER PUBLICATIONS

Chao et al., J. Lab. Clin. Med., 1996, 127(6): 612-620.*
Schechter et al., Reaction of Human Chymase with Reactive Site Variants of alpha 1-Antichymotrypsin, Journal of Biological Chemistry, 1993, 268(31): 23626-23633.*
Rubin et al., Cloning, Expression, Purification and Biological Activity of Recombinant Native and Variant Human alpha1-Antichymotrypsins, Journal of Biological Chemistry, 1990, 265(2): 1199-1207.*
WNgo et al., in The Protein Folding Problem and Tertiary Structure Prediction, 1994, Merz et al. (ed.), Birkhauser, Boston, MA, pp. 433 and 492-495.*
Chagas et al. (Determinants of the unusual cleavage specificity of lysyl-bradykinin releasing Kallikreins, Biochem. J., 1995, 306, pp. 63-69).*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Cloutier, Sylvain M. et al., "Development of recombinant inhibitors specific to human kallikrein 2 using phage-display selected substrates," Eur. J. Biochem., vol. 271:607-613 (2004).
Cloutier, Sylvain M. et al., "Substrate specificity of human kallikrein 2 (hK2) as determined by phage display technology," Eur. J. Biochem., vol. 269:2747-2754 (2002).
Deperthes, David, "Phage Display Substrate: A Blind Method for Determining Protease Specificity," Biol. Chem., vol. 383:1107-1112 (2002).
Bos, Ineke G.A. et al., "Effect of reactive site loop elongation on the inhibitory activity of C1-inhibitor," Biochimica et Biophysica Acta, vol. 1699:139-144 (2004).
Janciauskiene, Sabina, "Conformational properties of serine proteinase inhibitors (serpins) confer multiple pathophysiological roles," Biochimica et Biophysica Acta, vol. 1535:221-235 (2001).
International Preliminary Report on Patentability for Application No. PCT/IB2004/001040, 14 pages, dated Sep. 29, 2005.
International Search Report and Written Opinion for Application No. PCT/IB2004/001040, 11 pages, dated Oct. 12, 2004.

* cited by examiner

*Primary Examiner* — Suzanne M Noakes
*Assistant Examiner* — Jae W Lee
(74) *Attorney, Agent, or Firm* — Nelson Mullins Riley & Scarborough LLP; Jill Gorny Sloper, Esq.

(57) ABSTRACT

The present invention relates to a chimeric inhibitor protein of a protease comprising an inhibiting polypeptidic sequence and at least one polypeptidic sequence of a substrate-enzyme interaction site specific for a protease. Other objects of the invention are to provide a purified and isolated DNA sequence encoding the chimeric inhibitor protein of a protease, an expression vector characterized in that it comprises said purified and isolated DNA sequence, a eukaryotic or prokaryotic host cell transformed with this expression vector and a method of producing a chimeric inhibitor protein.

14 Claims, 15 Drawing Sheets

FIG. 3
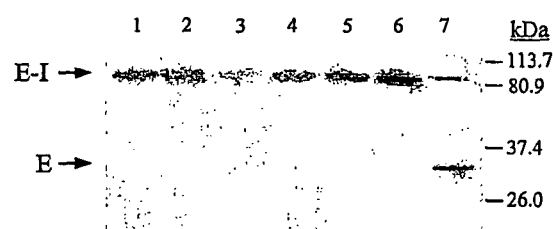
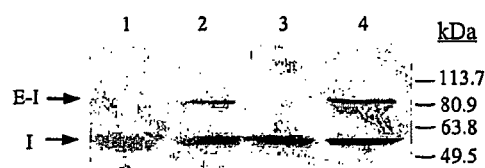
FIG. 4
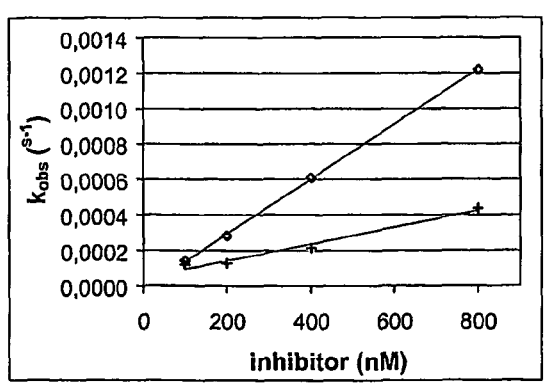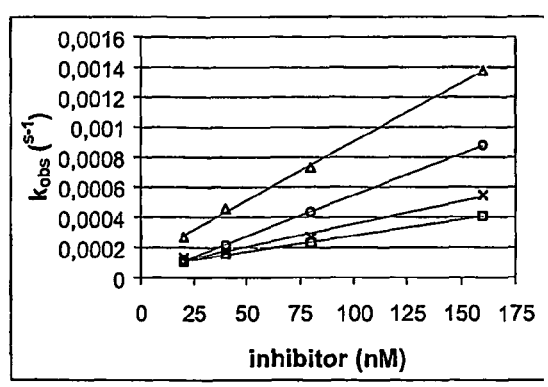

FIG. 7A

Italic : start codon ATG
Bold : His-tag
Underlined : DNA sequence different to ACTwt sequence
Underlined and grey : DNA sequence encoding RSL mutation.

DNA Sequence ACT variants : MD 820

SEQ ID N°1

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACCCTCCGTTCTCGAGCAGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variants : MD 820

SEQ ID N°2

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITLRSRAVETRTIVRF
NRPFLMIIVPTDTQNIFFMSKVTNPKQA*

FIG. 7B

Italic : start codon ATG
Bold : His-tag
Underlined : DNA sequence different to ACTwt sequence
Underlined and grey : DNA sequence encoding RSL mutation.

DNA Sequence ACT variant : MD 62

SEQ ID N°3

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACCAGGAGGTCTATCGATGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant : MD 62

SEQ ID N°4

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITRRSIDVETRTIVRF
NRPFLMIIVPTDTQNIFFMSKVTNPKQA*

FIG. 7C

Italic : start codon ATG
Bold : His-tag
Underlined : DNA sequence different to ACTwt sequence
Underlined and grey : DNA sequence encoding RSL mutation.

DNA Sequence ACT variant : MD 83

SEQ ID N°5

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCAGGGGGAGATCTGAGTTAGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant : MD 83

SEQ ID N°6

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIRGRSELVETRTIVRF
NRPFLMIIVPTDTQNIFFMSKVTNPKQA*

FIG. 7D

Italic : start codon ATG
Bold : His-tag
Underlined : DNA sequence different to ACTwt sequence
Underlined and grey : DNA sequence encoding RSL mutation.

DNA Sequence ACT variant : MD 67

SEQ ID N°7

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCA<u>AG</u>CTTAGAACA<u>A</u>CATTAGTGGAGAC<u>GC</u>GTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant: MD 67

SEQ ID N°8

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKI<u>KLRTT</u>LVETRTIVRF
NRPFLMIIVPTDTQNIFFMSKVTNPKQA*

FIG. 7E

Italic : start codon ATG
Bold : His-tag
Underlined : DNA sequence different to ACTwt sequence
Underlined and grey : DNA sequence encoding RSL mutation.

DNA Sequence ACT variant : MD 61

SEQ ID N°9

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCATGACAAGATCTAACGCAGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variant : MD 61

SEQ ID N°10

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIMTRSNAVETRTIVRF
NRPFLMIIVPTDTQNIFFMSKVTNPKQA*

FIG. 7F

Italic : start codon ATG
Bold : His-tag
Underlined : DNA sequence different to ACTwt sequence
Underlined and grey : DNA sequence encoding RSL mutation.

DNA Sequence ACT variants : MD 518

SEQ ID N°11

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACC<u>GAGCGTGTCTCGCCC</u>GTGGAGAC<u>GCG</u>TACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variants: MD 518

SEQ ID N°12

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKIT<u>ERVSP</u>VETRTIVRF
NRPFLMIIVPTDTQNIFFMSKVTNPKQA*

FIG. 7G

Italic : start codon ATG
Bold : His-tag
Underlined : DNA sequence different to ACTwt sequence
Underlined and grey : DNA sequence encoding RSL mutation.

DNA Sequence ACT variants : MDCI

SEQ ID N°13

*ATG*AGAGGATCCCATCACCATCACCATCACTCTAGACACCCTAACAGCCCACTTGACGAGGAGA
ATCTGACCCAGGAGAACCAAGACCGAGGGACACACGTGGACCTCGGATTAGCCTCCGCCAACGT
GGACTTCGCTTTCAGCCTGTACAAGCAGTTAGTCCTGAAGGCCCCTGATAAGAATGTCATCTTC
TCCCCACTGAGCATCTCCACCGCCTTGGCCTTCCTGTCTCTGGGGGCCCATAATACCACCCTGA
CAGAGATTCTCAAAGGCCTCAAGTTCAACCTCACGGAGACTTCTGAGGCAGAAATTCACCAGAG
CTTCCAGCACCTCCTGCGCACCCTCAATCAGTCCAGCGATGAGCTGCAGCTGAGTATGGGAAAT
GCCATGTTTGTCAAAGAGCAACTCAGTCTGCTGGACAGGTTCACGGAGGATGCCAAGAGGCTGT
ATGGCTCCGAGGCCTTTGCCACTGACTTTCAGGACTCAGCTGCAGCTAAGAAGCTCATCAACGA
CTACGTGAAGAATGGAACTAGGGGGAAAATCACAGATCTGATCAAGGACCTTGACTCGCAGACA
ATGATGGTCCTGGTGAATTACATCTTCTTTAAAGCCAAATGGGAGATGCCCTTTGACCCCCAAG
ATACTCATCAGTCAAGGTTCTACTTGAGCAAGAAAAAGTGGGTAATGGTGCCCATGATGAGTTT
GCATCACCTGACTATACCTTACTTCCGGGACGAGGAGCTGTCCTGCACCGTGGTGGAGCTGAAG
TACACAGGCAATGCCAGCGCACTCTTCATCCTCCCTGATCAAGACAAGATGGAGGAAGTGGAAG
CCATGCTGCTCCCAGAGACCCTGAAGCGGTGGAGAGACTCTCTGGAGTTCAGAGAGATAGGTGA
GCTCTACCTGCCAAAGTTTTCCATCTCGAGGGACTATAACCTGAACGACATACTTCTCCAGCTG
GGCATTGAGGAAGCCTTCACCAGCAAGGCTGACCTGTCAGGGATCACAGGGGCCAGGAACCTAG
CAGTCTCCCAGGTGGTCCATAAGGCTGTGCTTGATGTATTTGAGGAGGGCACAGAAGCATCTGC
TGCCACCGCGGTCAAAATCACCTTTAGATCTGCATTAGTGGAGACGCGTACCATTGTGCGTTTC
AACAGGCCCTTCCTGATGATCATTGTCCCTACAGACACCCAGAACATCTTCTTCATGAGCAAAG
TCACCAATCCCAAGCAAGCCTAA

Protein Sequence ACT variants: MD CI

SEQ ID N°14

MRGSHHHHHHSRHPNSPLDEENLTQENQDRGTHVDLGLASANVDFAFSLYKQLVLKAPDKNVIF
SPLSISTALAFLSLGAHNTTLTEILKGLKFNLTETSEAEIHQSFQHLLRTLNQSSDELQLSMGN
AMFVKEQLSLLDRFTEDAKRLYGSEAFATDFQDSAAAKKLINDYVKNGTRGKITDLIKDLDSQT
MMVLVNYIFFKAKWEMPFDPQDTHQSRFYLSKKKWVMVPMMSLHHLTIPYFRDEELSCTVVELK
YTGNASALFILPDQDKMEEVEAMLLPETLKRWRDSLEFREIGELYLPKFSISRDYNLNDILLQL
GIEEAFTSKADLSGITGARNLAVSQVVHKAVLDVFEEGTEASAATAVKITFRSALVETRTIVRF
NRPFLMIIVPTDTQNIFFMSKVTNPKQA*

Figure 8

| Serpin | Sequences | P6 | P5 | P4 | P3 | P2 | P1 | P'1 | P'2 | P'3 | P'4 | P'5 |
|---|---|---|---|---|---|---|---|---|---|---|---|---|
| ACT<sub>WT</sub> | Protein (a.a) SEQ ID N° 15 | V | K | I | T | L | L* | S | A | L | V | E |
| | DNA (codon) SEQ ID NO: 69 | GTC | AAA | ATC | ACC | CTC | CTT | TCT | GCA | TTA | GTG | GAG |
| MD820 | Protein (a.a) SEQ ID N° 16 | V | K | I | T | L | R* | S | R | A | V | E |
| | DNA (codon) SEQ ID NO: 70 | GTC | AAA | ATC | ACC | CTC | CGT | TCT | CGA | GCA | GTG | GAG |
| MD62 | Protein (a.a) SEQ ID N° 17 | V | K | I | T | R | R* | S | I | D | V | E |
| | DNA (codon) SEQ ID NO: 71 | GTC | AAA | ATC | ACC | AGG | AGG | TCT | ATC | GAT | GTG | GAG |
| MD83 | Protein (a.a) SEQ ID N° 18 | V | K | I | R | G | R* | S | E | L | V | E |
| | DNA (codon) SEQ ID NO: 72 | GTC | AAA | ATC | AGG | GGG | AGA | TCT | GAG | TTA | GTG | GAG |
| MD67 | Protein (a.a) SEQ ID N° 19 | V | K | I | K | L | R* | T | T | L | V | E |
| | DNA (codon) SEQ ID NO: 73 | GTC | AAA | ATC | AAG | CTT | AGA | ACA | ACA | TTA | GTG | GAG |
| MD61 | Protein (a.a) SEQ ID N° 20 | V | K | I | M | T | R* | S | N | A | V | E |
| | DNA (codon) SEQ ID NO: 74 | GTC | AAA | ATC | ATG | ACA | AGA | TCT | AAC | GCA | GTG | GAG |
| MD518 | Protein (a.a) SEQ ID N° 21 | V | K | I | T | E | R* | V | S | P | V | E |
| | DNA (codon) SEQ ID NO: 75 | GTC | AAA | ATC | ACC | GAG | CGT | GTC | TCG | CCC | GTG | GAG |
| MDCI | Protein (a.a) SEQ ID N° 22 | V | K | I | T | F | R* | S | A | L | V | E |
| | DNA (codon) SEQ ID NO: 76 | GTC | AAA | ATC | ACC | TTT | AGA | TCT | GCA | TTA | GTG | GAG |

FIG. 10 B
Control
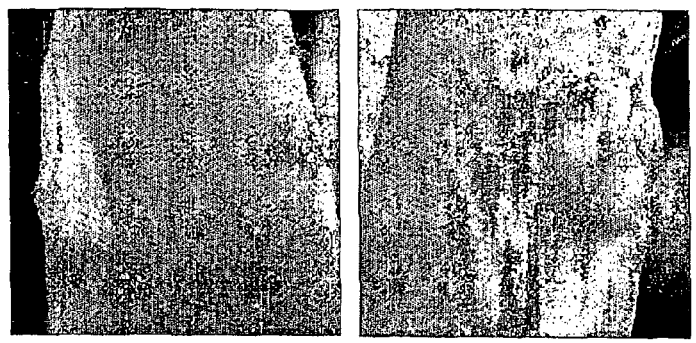
ACT-WT (50ug)
MD 67 (25ug)
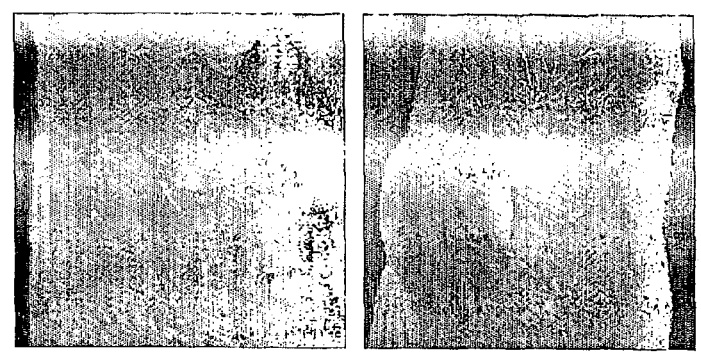
MD 67 (5ug)

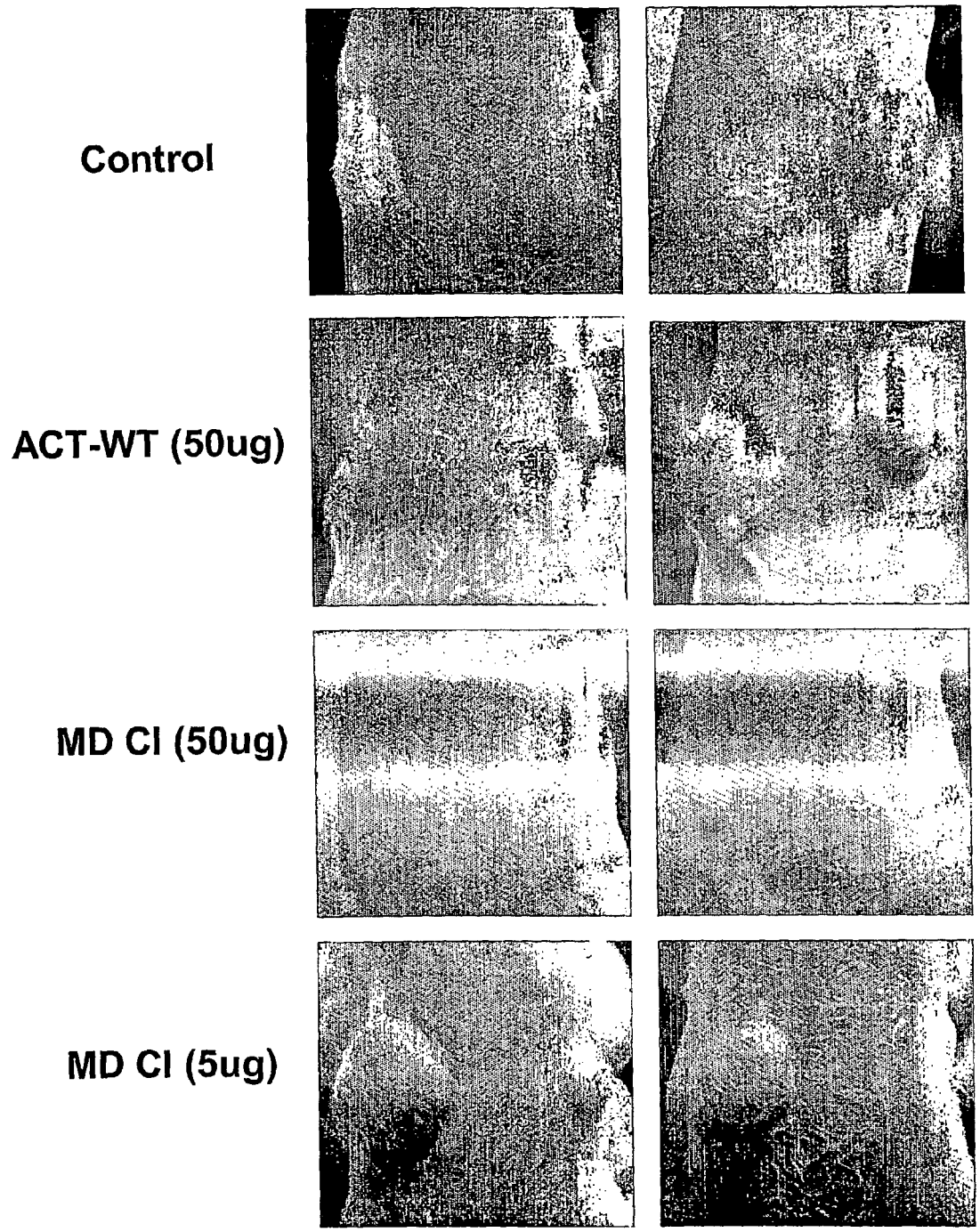

INHIBITOR PROTEINS OF A PROTEASE AND USE THEREOF

RELATED APPLICATIONS

This application is a 35 U.S.C. §371 filing of International Application Number PCT/IB2004/001040 which was filed Apr. 5, 2004, which claims priority to U.S. Provisional Application No. 60/460,345, filed on Apr. 4, 2003. The contents of the aforementioned applications are hereby incorporated herein by reference.

FIELD OF THE INVENTION

The present invention relates to a chimeric inhibitor protein of a protease comprising an inhibiting polypeptidic sequence and at least one polypeptidic sequence of a substrate-enzyme interaction site specific for a protease.

Other objects of the invention are to provide a purified and isolated DNA sequence encoding the chimeric inhibitor protein of a protease, an expression vector characterized in that it comprises said purified and isolated DNA sequence, a eukaryotic or prokaryotic host cell transformed with this expression vector and a method of producing a chimeric inhibitor protein.

BACKGROUND OF THE INVENTION

Of all proteins expressed by living organisms, proteases are among the most critical in mediating pathways of cell life and death. In fact, the initial interactions between protease and substrate and subsequent cleavage lie at the base of a vast spectrum of essential biological events including thrombosis, coagulation and apoptosis.

Dysregulated proteolysis, or imbalance between proteases and antiproteases, has been searched intensively based on the suspicion that it could be a key factor in many pathologies where proteases have been involved such as cancer, autoimmune diseases, inflammation and infectious diseases. Different studies done with antiproteolytic agents in cancer and inflammatory disease (such as rheumatoid arthritis and emphysema) models have also shown interesting outcome improvement, strengthening the antiproteolytic therapy and the role of balance between proteases and antiproteases.

For example, in prostate cancer, which is one of the most common diagnosed cancers in American men, proteases are believed to play a pivotal role in the malignant behaviour of cancer cells including rapid tumor growth, invasion, and metastasis.

Human glandular kallikrein (hK2) protein is a trypsin-like serine protease expressed predominantly in the prostate epithelium. Firstly isolated from human seminal plasma, hK2 has recently emerged as a diagnostic marker for prostate cancer (Deperthes et al. 1995 "Isolation of prostatic kallikrein hK2, also known as hGK-1, in human seminal plasma" *Biochim Biophys Acta* 1245, 311-6).

Beside its role as marker, its proteolytic activities suggest that hK2 could contribute to cancer progression. Several potential functions for this enzyme have been proposed, including the activation of urokinase-type plasminogen activator and inactivation of plasminogen activator inhibitor-1, activation of pro-PSA, degradation of fibronectin and degradation of insulin-like growth factor binding protein (IGF-BP) (for review see Cloutier et al., 2004 "Development of recombinant inhibitors specific to human kallikrein 2 using phase-display selected substrates" *Eur J Biochem* 3, 607-13).

It has recently been shown that kallikrein hK2 can form a specific complex with a protease inhibitor, known as PI-6, in cancers and particularly in prostate cancer. Based on the discovery of this specific complex, U.S. Pat. Nos. 6,284,873 and 6,472,143 provide a diagnostic method for determining the presence or absence of cancer or tissue necrosis.

Taking into account its prostate tissue specific expression and the involvement of all its potential substrates in cancer development, hK2 is also considered as a potential therapeutic target (Darson et al. 1997 "Human glandular kallikrein 2 (hK2) expression in prostatic intraepithelial neoplasia and adenocarcinoma: a novel prostate cancer marker" *Urology* 49, 857-62). Therefore, the development of specific and long-lasting protease inhibitors and especially kallikrein inhibitors would be useful.

These Protease inhibitor candidates can be selected among the serpin (serine protease inhibitors) family, which is a large family of proteins implicated in the regulation of complex physiological processes. These proteins of about 45 kDa can be subdivided into two groups, one being inhibitory and the other non-inhibitory.

Serpins contain an exposed flexible reactive-site loop or reactive-serpin loop (RSL), which is implicated in the interaction with the putative target proteinase. Following the binding to the enzyme and cleavage of the P1-P1' scissile bond of the RSL, a covalent complex is formed (Huntington et al. 2000 "Structure of a serpin-protease complex shows inhibition by deformation" *Nature* 407, 923-6). Formation of this complex induces a major conformational rearrangement and thereby traps irreversibly the target protease. The inhibitory specificity of serpins is largely attributed to the nature of the residues at P1-P'1 positions and the length of the RSL. Changing the RSL domain or the reactive site of serpins is one approach to understand the inhibitory process between a serpin and an enzyme and to develop specific inhibitors (Dufour et al. 2001 "The contribution of arginine residues within the P6-P1 region of alpha 1-antitrypsin to its reaction with furin" *J Biol Chem* 276, 38971-9 and Plotnick et al. 2002 "The effects of reactive site location on the inhibitory properties of the serpin alpha(1)-antichymotrypsin" *J Biol Chem* 277, 29927-35).

Several serpins such as protein C inhibitor, α2 antiplasmin, antithrombin-III, α1-antichymotrypsin (ACT), or protease inhibitor 6 have been identified as hK2 inhibitors (Saedi et al. 2001 "Human kallikrein 2 (hK2), but not prostate-specific antigen (PSA), rapidly complexes with protease inhibitor 6 (PI-6) released from prostate carcinoma cells" *Int J Cancer* 94, 558-63). The relatively slow complex formation between hK2 and ACT is mainly attributed to residues Leu 358-Ser 359 at P1-P'1 positions of the RSL, an unfavourable peptide bond for this trypsin-like enzyme.

Up to now, only selections of new kallikrein inhibitors, which specifically inhibit plasma kallikrein, and use thereof in therapeutic and diagnostic methods have been disclosed (patents U.S. Pat. No. 6,057,287, U.S. Pat. No. 6,333,402, U.S. Pat. No. 5,994,125, and U.S. Pat. No. 5,795,865). However, these patents describe the production of inhibitors that are homologous to bovine pancreatic trypsin inhibitor Kunitz domains, and especially proteins that are homologous to lipoprotein-associated coagulation inhibitor (LACI) Kunitz domains, which specifically inhibit plasma kallikreins.

Besides being specific for plasma kallikrein, these inhibitors are quite small molecules and bind to plasma kallikrein in a reversible manner. One of the major drawback of this approach is that the use of proteins inhibiting their targets in a reversible manner bears the risk that decomplexation of the protease restores its activity.

Therefore, one advantage of using larger inhibitors, as described herein, is that this leads to the formation of covalent complexes which inhibits the protease target in an irreversible manner. A further advantage of the present invention is that large covalent complexes are known to be quickly eliminated from circulation.

SUMMARY OF THE INVENTION

Therefore, the object of the present invention is to provide a protease inhibitor protein with high specificity for said protease and use thereof in a pharmaceutical composition. This inhibitor protein is chimeric insofar as it comprises an inhibiting polypeptidic sequence and at least one polypeptidic sequence of a substrate-enzyme interaction site specific for a protease.

An other object of the invention is to provide a purified and isolated DNA sequence encoding the chimeric inhibitor protein of a protease, an expression vector characterized in that it comprises said purified and isolated DNA sequence and a eukaryotic or prokaryotic host cell transformed with this expression vector.

A further object of the present invention is to provide a method for producing the chimeric inhibitor protein of a protease. This method comprises the steps of
a) selecting a polynucleotidic sequence encoding a substrate-enzyme interaction site specific for a protease,
b) introducing said polynucleotidic sequence into a sequence encoding an inhibitor protein of a serine or cysteine protease, so as to obtain a chimeric sequence,
c) allowing expression of said chimeric sequence in a cell expression system under suitable conditions,
d) and recovering the chimeric inhibitor protein of a protease.

BRIEF DESCRIPTION OF THE FIGURES

FIGS. 3 A and B show the formation of complex between hK2 and recombinant inhibitors. Arrows indicate hK2 (E), inhibitor (I), and hK2-ACT complex (E-I).

FIGS. 4 A and B show the inhibition of hK2 by $rACT_{WT}$ and its variants under pseudo-first order conditions. The interaction of hK2 and recombinant serpins was measured under pseudo-first order conditions using progress curve method.

FIG. 7A shows the DNA and protein sequences of MD820
FIG. 7B shows the DNA and protein sequences of MD62
FIG. 7C shows the DNA and protein sequences of MD83
FIG. 7D shows the DNA and protein sequences of MD67
FIG. 7E shows the DNA and protein sequences of MD61
FIG. 7F shows the DNA and protein sequences of MD518
FIG. 7G shows the DNA and protein sequences of MDCI
FIG. 8 represents a comparison of RSL sequences of ACT and MD inhibitors. Plain type residues are common to $ACT_{WT}$, bold and underlined residues correspond to mutation in RSL of ACT variants. The putative cleavage site in serpins is marked by asterisks between the P1-P1' residues.

FIG. 11 shows the inhibition of tumor growth by MD CI. Prostate cancer cells DU-145 ($3\times10^6$ cells), transfected with human kallikrein 2, were implanted in nude mice and then treated with MD CI (5 or 50 kg/injection).

DETAILED DESCRIPTION OF THE INVENTION

Figure 1:
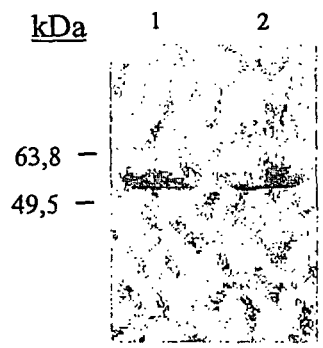
FIG. 1 represents an SDS-PAGE analysis under reducing conditions of purified recombinant ACT. Variant 6.1 (lane 1) and wild type ACT (lane 2).

The present invention relates to a chimeric inhibitor protein of a protease comprising an inhibiting polypeptidic sequence and at least one polypeptidic sequence of a substrate-enzyme interaction site specific for said protease.

"Chimeric inhibitor protein" refers to a protein comprising two or more polypeptides, which are from different origins, i.e. which do not occur together in the nature.

As used herein, the terms "protein", "polypeptide", "polypeptidic", "peptide" and "peptidic" are used interchangeably herein to designate a series of amino acid residues connected to the other by peptide bonds between the alpha-amino and carboxy groups of adjacent residues.

The chimeric protein of the invention is an inhibitor of a protease and is composed of an inhibiting polypeptidic sequence and of, at least, one polypeptidic sequence of a substrate-enzyme interaction site specific for said protease. The polypeptidic sequence of a substrate-enzyme interaction site confers highly selective properties of the inhibitor towards a particular protease and this polypeptidic sequence is selected on the basis of the protease to be inhibited.

Typically, this polypeptidic sequence of a substrate-enzyme interaction site can be a substrate active site sequence. "Substrate active site sequence" refers to a sequence found on a substrate and which is a preferential recognition site for a protease. Recognition of the substrate active site sequence by a protease can lead to the activation, inactivation or degradation of the substrate and most of the time this high affinity interaction involves the recognition not only of a specific sequence but also of its 3-D conformation.

Encompassed by the present invention is also a molecular chimera of the substrate active site sequence. By "molecular chimera" is intended a polynucleotide sequence that may include a functional portion of the substrate active site sequence and that will be obtained, for example, by protein chemistry techniques known by those skilled in the art.

Particular combinations of the substrate active site sequence or fragments or subportions thereof are also considered in the present invention.

"Fragments" refer to sequences sharing at least 40% amino acids in length with the respective sequence of the substrate active site. These sequences can be used as long as they exhibit the same properties as the native sequence from which they derive. Preferably these sequences share more than 70%, preferably more than 80%, in particular more than 90% amino acids in length with the respective sequence the substrate active site.

These fragments can be prepared by a variety of methods and techniques known in the art such as for example chemical synthesis.

The present invention also includes variants of the substrate active site sequence. The term "variants" refer to polypeptides having amino acid sequences that differ to some extent from a native sequence polypeptide, that is amino acid sequences that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Conservative amino acid substitutions are herein defined as exchanges within one of the following five groups:
I. Small aliphatic, nonpolar or slightly polar residues: Ala, Ser, Thr, Pro, Gly
II. Polar, positively charged residues: His, Arg, Lys
III. Polar, negatively charged residues: and their amides: Asp, Asn, Glu, Gln
IV. Large, aromatic residues: Phe, Tyr, Trp
V. Large, aliphatic, nonpolar residues: Met, Leu, Ile, Val, Cys.

Preferably the substrate of the present invention is a serpin, in this case the substrate active site sequence may be a Reactive Serpin Loop sequence, fragments thereof, a molecular chimera thereof, a combination thereof and/or variants thereof.

"Reactive Serpin Loop" or "Reactive Site Loop" or RSL refers to an exposed flexible reactive-site loop found in serpin and which is implicated in the interaction with the putative target protease. From the residue on the amino acid side of the scissile bond, and moving away from the bond, residues are conventionally called P1, P2, P3, etc. Residues that follow the scissile bond are called P1', P2', P3', etc. Usually, the RSL is composed of 6 to 12 amino acid residues.

This RSL sequence can be selected from the group comprising the SEQ ID No 16, 17, 18, 19, 20, 21 and 22, fragments thereof, molecular chimeras thereof, combinations thereof and/or variants thereof.

RSL sequence may also be selected among the following possibilities shown in table I.

TABLE I

Positions in the RSL which can be changed

POSITION IN THE REACTIVE SITE LOOP

| P5 | P4 | P3 | P2 | P1 | P*1 | P*2 | P*3 | P*4 | SEQ ID NO: |
|----|----|----|----|----|-----|-----|-----|-----|------------|
|    |    | S  | S  | R  | T   | E   |     |     | 23 |
|    |    | K  | T  | R  | S   | N   |     |     | 24 |
|    | I  | S  | P  | R  | S   |     |     |     | 25 |
|    | G  | V  | F  | R  | S   |     |     |     | 26 |
|    | G  | T  | V  | R  | S   |     |     |     | 27 |
|    | E  | T  | K  | R  | S   |     |     |     | 28 |
|    |    | L  | G  | R  | S   | L   |     |     | 29 |
|    |    | R  | G  | R  | S   | E   |     |     | 30 |
|    |    | R  | R  | R  | S   | I   | D   |     | 31 |
|    |    | V  | L  | R  | S   | P   |     |     | 32 |
|    |    | P  | F  | R  | S   | S   |     |     | 33 |
|    |    |    | R  | R  | S   | G   | S   | V   | 34 |
|    | A  | R  | A  | R  | S   |     |     |     | 35 |
|    |    | S  | D  | R  | T   | A   |     |     | 36 |
|    |    | K  | L  | R  | T   | T   |     |     | 37 |
|    |    |    | R  | R  | A   | A   | M   | M   | 38 |
|    |    |    | R  | R  | A   | P   | M   |     | 39 |
|    |    | D  | V  | R  | A   | A   |     |     | 40 |
|    |    | P  | G  | R  | A   | P   |     |     | 41 |
|    | V  | E  | S  | R  | A   |     |     |     | 42 |
|    |    | A  | R  | R  | A   | S   | E   |     | 43 |
|    | T  | L  | Q  | R  | V   |     |     |     | 44 |
|    | R  | L  | E  | R  | V   |     |     |     | 45 |
|    |    |    | E  | R  | V   | S   | P   |     | 46 |
|    | S  | S  | P  | R  | V   |     |     |     | 47 |

TABLE I-continued

Positions in the RSL which can be changed

POSITION IN THE REACTIVE SITE LOOP

| P5 | P4 | P3 | P2 | P1 | P*1 | P*2 | P*3 | P*4 | SEQ ID NO: |
|----|----|----|----|----|-----|-----|-----|-----|------------|
|    |    |    |    | R  | V   | G   | P   | Y   | 48 |
|    |    | P  | S  | A  | R   | M   |     |     | 49 |
|    |    |    | R  | G  | R   | M   | A   |     | 50 |
|    |    |    | T  | V  | R   | M   | P   |     | 51 |
|    |    |    |    | L  | R   | M   | P   | T   | 52 |
|    |    |    |    | H  | R   | M   | S   | S   | 53 |
|    |    |    |    | R  | P   | Q   | E   | L   | 54 |
|    |    |    | V  | R  | P   | L   | E   |     | 55 |
|    |    |    | S  | G  | R   | L   | A   |     | 56 |
|    |    | G  | T  | L  | R   | F   |     |     | 57 |
|    |    | Q  | W  | R  | N   | S   |     |     | 58 |
|    |    |    |    | R  | N   | D   | K   | L   | 59 |
|    |    |    | M  | R  | N   | R   | A   |     | 60 |
|    |    |    | T  | R  | D   | S   | R   |     | 61 |
|    | T  | G  | S  | R  | D   |     |     |     | 62 |
|    | I  | M  | S  | R  | Q   |     |     |     | 63 |
|    | E  | Q  | H  | R  | Q   | M   | G   |     | 64 |
| L  | T  | T  | S  | K  |     |     |     |     | 65 |
|    | P  | F  | R  | K  | I   |     |     |     | 66 |
|    |    | M  | T  | R  | S   | N   |     |     | 67 |
|    |    |    | L  | R  | S   | R   | A   |     | 68 |

Amino acid sequence of P4-P3' residues in RSL (Reactive Serpin Loop) corresponding to potential substrate peptide
Blank spaces indicate that there is no modification needed in order to obtain substrate specificity to hK2.

Usually the protease is selected from the group comprising kallikrein, chymotrypsin (Chtr), urokinase (uPA) and human neutrophile elastase (FIN) enzymes. Preferably, the protease is a human kallikrein, most preferably this human kallikrein is hK2 (also known as hGK-1).

HK2 belongs to the kallikrein gene family which is composed of 15 members but only the Prostate Specific Antigen (PSA or hK3) and hK2 are expressed at a high level by the prostate. One of the potential physiologic role of hK2 is the proteolytic degradation of the sperm-entrapping gel formed immediately after ejaculation, particularly the cleavage of semenogelins and fibronectin. In addition, it was demonstrated in an in vitro test that hK2 can enhance insulin-like growth factor's (IGF) mitogenic action by IGF binding protein hydrolysis. In vitro studies also showed that hK2 activates prourokinase, generate bradykinin-like substances from kininogens (potential cross-activation of EGF-receptors via B2 bradykinin receptors) and converts proPSA into an active form. These hK2 activities represent arguments in favor of a potential role of hK2 in extracellular matrix protein degradation and consequently detachment and migration of prostate cancer cells. In addition, hK2 could enhance prostate cancer development by release of mitogenic factor and activation of growth receptors.

In case the protease to be inhibited is a cystein protease, then this protease is selected from the group comprising cathepsins (K, L, and S subtypes), the prohormone thiol proteinase and the caspase family (Caspases 1, 3, 4, and 8).

Cystein proteases, which are proteolytic enzymes that utilize a cystein residue for their catalytic activity, can be grouped in at least 30 protein families. Each family contains proteins with similar amino acid sequences and evolutionarily conserved sequence motifs which reflects the family member's similar 3D structures.

The inhibiting polypeptidic sequence of the chimeric inhibitor protein is usually a serine or a cysteine protease.

In the case the inhibiting polypeptidic sequence is from a serine protease then this inhibiting polypeptidic sequence is preferably a serpin sequence, fragments thereof, a molecular chimera thereof, a combination thereof and/or variants thereof.

This serpin sequence can be selected from the group comprising the α-1antichymotrypsin (ACT), protein C inhibitor (PCI), α-1antiproteinase (AAT), human α-1antitrypsin-related protein precursor (ATR), α-2-plasmin inhibitor (AAP), human anti-thrombin-III precursor (ATIII), protease inhibitor 10 (PI10), human collagen-binding protein 2 precursor (CBP2), protease inhibitor 7 (PI7), protease inhibitor leuserpin 2 (HLS2), human plasma protease C1 inhibitor (C1 INH), monocyte/neutrophil elastase inhibitor (M/NEI), plasminogen activator inhibitor-3 (PAI3), protease inhibitor 4 (PI4), protease inhibitor 5 (PI5), protease inhibitor 12 (PI12), human plasminogen activator inhibitor-1 precursor endothelial (PAI-1), human plasminogen activator inhibitor-2 placental (PAI2), human pigment epithelium-derived factor precursor (PEDF), protease inhibitor 6 (PI6), protease inhibitor 8 (PI8), protease inhibitor 9 (PI9), human squamous cell carcinoma antigen 1 (SCCA-1), human squamous cell carcinoma antigen 2 (SCCA-2), T4-binding globulin (TBG), Megsin, and protease inhibitor 14 (PI14), fragments thereof, molecular chimeras thereof, combinations thereof and/or variants thereof.

Since most of these serpins have different names, we include below a table summarizing their specifications:

TABLE II

| Serpin | Accession Number | RSL sequence |
|---|---|---|
| PI or AAT, A1AT_HUMAN ALPHA-1-ANTITRYPSIN PRECURSOR (ALPHA-1 PROTEASE INHIBITOR) (ALPHA-1-ANTIPROTEINASE) | sp\|P01009\| | GTEAAGAMFLEAIPMSIPPE (SEQ ID NO: 77) |
| PIL or ATR, A1AU_HUMAN ALPHA-1-ANTITRYPSIN-RELATED PROTEIN PRECURSOR | sp\|P20848\| | GTEATGAPHLEEKAWSKYQT (SEQ ID NO: 78) |
| PLI OR AAP, A2AP_HUMAN ALPHA-2-ANTIPLASMIN PRECURSOR (ALPHA-2-PLASMIN INHIBITOR) (ALPHA-2-PI) (ALPHA-2-AP) | sp\|P08697\| | GVEAAAATSIAMSRMSLSSF (SEQ ID NO: 79) |
| AACT, AACT_HUMAN ALPHA-1-ANTICHYMOTRYPSIN PRECURSOR (ACT) | sp\|P01011\| | GTEASAATAVKITLLSALVE (SEQ ID NO: 80) |
| AT3, ANT3_HUMAN ANTITHROMBIN-III PRECURSOR (ATIII) | sp\|P01008\| | GSEAAASTAVVIAGRSLNPN (SEQ ID NO: 81) |
| PI10, BOMA_HUMAN BOMAPIN (PROTEASE INHIBITOR 10) | sp\|P48595\| | GTEAAAGSGSEIDIRIRVPS (SEQ ID NO: 82) |
| CBP2, CBP2_HUMAN COLLAGEN-BINDING PROTEIN 2 PRECURSOR (COLLIGIN 2) | sp\|P50454\| | GNPFDQDIYGREELRSPKLF (SEQ ID NO: 83) |
| PI7 or PN1 GDN_HUMAN GLIA DERIVED NEXIN PRECURSOR (GDN) (PROTEASE NEXIN I) (PN-1) (PROTEASE INHIBITOR 7) | sp\|P07093\| | GTKASAATTAILIARSSPPW (SEQ ID NO: 84) |
| HCF2, HEP2_HUMAN HEPARIN COFACTOR II PRECURSOR (HC-II) (PROTEASE INHIBITOR LEUSERPIN 2) (HLS2) | sp\|P05546\| | GTQATTVTTVGFMPLSTQVR (SEQ ID NO: 85) |
| C1NH or C1IN, IC1_HUMAN PLASMA PROTEASE C1 INHIBITOR PRECURSOR (C1 INH) | sp\|P05155\| | GVEAAASAISVARTLLVFE (SEQ ID NO: 86) |
| ELANH2 or PI2, ILEU_HUMAN LEUKOCYTE ELASTASE INHIBITOR (LEI) (MONOCYTE/NEUTROPHIL ELASTASE INHIBITOR) (M/NEI) (EI) | sp\|P30740\| | GTEAAAATAGIATFCMLMPE (SEQ ID NO: 87) |
| PCI or PLANH3 or PROCI, IPSP_HUMAN PLASMA SERINE PROTEASE INHIBITOR PRECURSOR (PCI) (PROTEIN C INHIBITOR) (PLASMINOGEN ACTIVATOR INHIBITOR-3) (PAI3) | sp\|P05154\| | GTRAAAATGTIFTFRSARLN (SEQ ID NO: 88) |
| PI4 or KST, KAIN_HUMAN KALLISTATIN PRECURSOR (KALLIKREIN INHIBITOR) (PROTEASE INHIBITOR 4) | sp\|P29622\| | GTEAAAATTFAIKFFSAQTN (SEQ ID NO: 89) |
| PI5, MASP_HUMAN MASPIN PRECURSOR (PROTEASE INHIBITOR 5) | sp\|P36952\| | GGDSIEVPGARILQHKDELN (SEQ ID NO: 90) |
| PI12, NEUS_HUMAN NEUROSERPIN PRECURSOR (PROTEASE INHIBITOR 12) | sp\|Q99574\| | GSEAAAVSGMIAISRMAVLY (SEQ ID NO: 91) |
| PAI1 or PLANH1, sp\|P05121\|PA\|1_HUMAN PLASMINOGEN ACTIVATOR INHIBITOR-1 PRECURSOR, ENDOTHELIAL (PAI-1) | sp\|P05121\| | GTVASSSTAVIVSARMAPEE (SEQ ID NO: 92) |
| PAI2 or PLANH2, PAI2_HUMAN PLASMINOGEN ACTIVATOR INHIBITOR-2, PLACENTAL (PAI-2) (MONOCYTE ARG- SERPIN) (UROKINASE INHIBITOR) | sp\|P05120\| | GTEAAAGTGGVMTGRTGHGG (SEQ ID NO: 93) |
| PEDF, PEDF_HUMAN PIGMENT EPITHELIUM-DERIVED FACTOR PRECURSOR (PEDF) (EPC-1) | sp\|P36955\| | GAGTTPSPGLQPAHLTFPLD (SEQ ID NO: 94) |

TABLE II-continued

| Serpin | Accession Number | RSL sequence |
| --- | --- | --- |
| PI6 or PTI, PTI6_HUMAN PLACENTAL THROMBIN INHIBITOR (CYTOPLASMIC ANTIPROTEINASE) (CAP) (PROTEASE INHIBITOR 6) | sp\|P35237\| | GTEAAATAAIMMMRCARFV (SEQ ID NO: 95) |
| PI8, PTI8_HUMAN CYTOPLASMIC ANTIPROTEINASE 2 (CAP2) (CAP-2) (PROTEASE INHIBITOR 8) | sp\|P50452\| | GTEAAATAVVRNSRCSRME (SEQ ID NO: 96) |
| PI9, PTI9_HUMAN CYTOPLASMIC ANTIPROTEINASE 3 (CAP3) (CAP-3) (PROTEASE INHIBITOR 9) | sp\|P50453\| | GTEAAAASSCFVVAECCMES (SEQ ID NO: 97) |
| SCCA1, SCC1_HUMAN SQUAMOUS CELL CARCINOMA ANTIGEN 1 (SCCA-1) (PROTEIN T4-A) | sp\|P29508\| | GAEAAAATAVVGFGSSPAST (SEQ ID NO: 98) |
| SCCA2, SCC2_HUMAN SQUAMOUS CELL CARCINOMA ANTIGEN 2 (SCCA-2) (LEUPIN) | sp\|P48594\| | GVEAAAATAVVVVELSSPST (SEQ ID NO: 99) |
| TBG, THBG_HUMAN THYROXINE-BINDING GLOBULIN PRECURSOR (T4-BINDING GLOBULIN) | sp\|P05543\| | GTEAAAVPEVELSDQPENTF (SEQ ID NO: 100) |
| MEGSIN | gi\|4505149\|ref\|NP_003775.1\| | GTEATAATGSNIVEKQLPQS (SEQ ID NO: 101) |
| PI14, pancpin, TSA2004 | gi\|3724282\|dbj\|BAA33766.1\| | GSEAATSTGIHIPVIMSLAQ (SEQ ID NO: 102) |

As an example of chimeric inhibitor proteins according to the invention, Applicants have surprisingly found 6 new chimeric inhibitor proteins specific for the protease hK2 as resumed below in table III, these inhibitors are:

TABLE III

| Chimeric inhibitors | Other name | SEQ ID N° (protein) |
| --- | --- | --- |
| $rACT_{8.20}$ | MD820 | 2 |
| $rACT_{6.2}$ | MD62 | 4 |
| $rACT_{8.3}$ | MD83 | 6 |
| $rACT_{6.7}$ | MD67 | 8 |
| $rACT_{6.1}$ | MD61 | 10 |
| $ACT_{5.18}$ | MD518 | 12 |

These chimeric inhibitor proteins have been obtained by modifying the RSL of α1-antichymotrypsin (rACT), which is known to inhibit a large panel of human enzymes such as chymotrypsin, mast cell chymase, cathepsin G, prostatic kallikreins hK2 and PSA (hK3), in order to change the specificity of this serpin. Peptide sequences, selected as substrates for the enzyme hK2 by phage display technology as explained in detail in Example 1, have been used to replace the scissile bond and neighbour amino acid residues of the RSL. Recombinant inhibitors were produced in bacteria and purified by affinity chromatography.

Compared to wild type rACT, which inhibited hK2 very slowly (12-16 h), the modified rACTs have been shown to form a covalent complex very quickly within few minutes. Three of the six rACT variants were specific to hK2 with high association constants (see tables V and VI). Incubating with an excess of inhibitors ($[I]_o/[E]_o$ of 100:1) for 30 minutes, hK2 is completely inhibited by $rACT_{6.2}$, $rACT_{8.3}$, $rACT_{6.7}$ and $rACT_{6.1}$, whereas $rACT_{8.20}$ and $rACT_{5.18}$ inhibited 95% and 73% of enzyme activity, respectively. Under this condition, wild type rACT showed no inhibition activity toward hK2. Among these variants, two ($rACT_{8.3}$ and $rACT_{5.18}$) are specific to hK2, inhibiting no other tested enzyme. Two other variants, $rACT_{6.7}$ and $rACT_{6.2}$, inhibited as well PK at 36% and 100% respectively. As wild-type ACT, variant $rACT_{8.20}$ inhibited the two chymotrypsin-like proteases Chtr and PSA but additionally also PK and HNE. None of the recombinant serpins showed inhibitory activity against the kallikrein hK1 and uPA.

Additionally, applicants have also found that replacing residues P3-P3' located in RSL structure of $rACT_{WT}$ by substrate pentapeptide coding for the RSL of Protein C inhibitor (PCI) lead to the production of a chimeric inhibitor (MDCI) which is able to inhibit kallikreins hK2 and hK3.

Therefore, the chimeric inhibitor of a protease may be selected from the group comprising MD820, MD62, MD61, MD67 and MDCI. Preferably this chimeric inhibitor protein is MD62 or MD61.

It is known that a Stoichiometry of Inhibition (SI) value superior to one is generally interpreted as substrate behaviour of serpin. In this scheme, after formation of an initial Michaelis complex and cleavage in the RSL, most of the complex is broken down into active enzyme and cleaved inhibitor which is definitively inactivated. Applicants have analyzed ACT variants-hK2 reactions for non complex forming cleavage of the inhibitor, incubating the samples at a 10:1 fold excess of inhibitor to protease. These conditions, close to or below calculated SI values of the tested ACT variants (see Table VI), normally favour proteolysis of serpins or serpin-protease complexes. Surprisingly, Applicants have observed a discrepancy to this hypothesis since degradation of variant ACTs by hK2 was not observed despite high SI values. Without wishing to be bound by the theory, a possible explanation for the lack of ACT degradation is the condition under which the SI determination was performed. Covalent ACTs-hK2 complexes are forming in vitro very slowly. This is in agreement with our observation that after 30 minutes incubation at 25° C. no inhibition of hK2 with wild-type ACT has been detected (Table V) and that even after prolonged incubation at 37° C., hK2 was only partially complexed with wild type ACT (FIG. 3).

Applicants have also assessed the specificity of these new inhibitors toward other proteases. The evaluation has been performed under the same conditions for all proteases (pseudo-physiological conditions) in order to ensure a better translation for further in vivo applications. The permutation of RSL cleavage site for hK2 phage display selected substrates has changed wild type ACT into highly sensitive inhibitors for hK2. In addition, two of these inhibitors showed a unique reactivity with hK2 and not with other studied enzymes known to target similar biological substrates, such as plasma kallikrein, hK1, PSA, urokinase (uPA), and human neutrophile elastase (HNE). To Applicants knowledge, this is the first report mentioning the development of a specific inhibitor for hK2.

Interestingly, rACT$_{8.20}$ (MD820) inhibits beside hK2 also chymotrypsin, and more weakly plasma kallikrein and human elastase, representing a broad inhibition specificity.

The inhibiting polypeptidic sequence of the chimeric inhibitor protein may also be selected from a cysteine protease since there are a now a number of well-documented instances of inhibition of cysteine proteases by serpins (Gettins P. G. W., 2002 "Serpin structure, mechanism, and function" in Chem. Rev, 102, 4751-4803). These examples include inhibition of cathepsins K, L and S by the serpin squamous cell carcinoma antigen1, inhibition of prohormone thiol proteinase by the α-1antichymotrypsin, and inhibition of members of the caspase family, including caspase 1 (interleukine 1β converting enzyme), caspase 3, and caspase 8 by the viral serpin crmA and caspases 1, 4 and 8 by the human serpin PI9.

When recombinant techniques are employed to prepare a chimeric inhibitor protein of a protease in accordance with the present invention, nucleic acid molecules or fragments thereof encoding the polypeptides are preferably used.

Therefore the present invention also relates to a purified and isolated DNA sequence encoding the chimeric inhibitor protein of a protease as described above.

"A purified and isolated DNA sequence" refers to the state in which the nucleic acid molecule encoding the chimeric inhibitor protein of a protease of the invention, or nucleic acid encoding such chimeric inhibitor protein of a protease will be, in accordance with the present invention. Nucleic acid will be free or substantially free of material with which it is naturally associated such as other polypeptides or nucleic acids with which it is found in its natural environment, or the environment in which it is prepared (e.g. cell culture) when such preparation is by recombinant DNA technology practised in vitro or in vivo.

DNA which can be used herein is any polydeoxynuclotide sequence, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid.

DNA sequences that encode the chimeric inhibitor protein of a protease, or a fragment thereof, can be synthesized by standard chemical techniques, for example, the phosphotri-ester method or via automated synthesis methods and PCR methods.

The purified and isolated DNA sequence encoding the chimeric inhibitor protein according to the invention may also be produced by enzymatic techniques. Thus, restriction enzymes, which cleave nucleic acid molecules at predefined recognition sequences can be used to isolate nucleic acid sequences from larger nucleic acid molecules containing the nucleic acid sequence, such as DNA (or RNA) that codes for the chimeric inhibitor protein or for a fragment thereof.

Encompassed by the present invention is also a nucleic acid in the form of a polyribonucleotide (RNA), including, e.g., single-stranded RNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

The purified and isolated DNA sequence encoding a chimeric inhibitor of a protease is preferably selected from the group comprising SEQ ID No 1, SEQ ID No 3, SEQ ID No 5, SEQ ID No 7, SEQ ID No 9, SEQ ID No 11 and SEQ ID No 13.

The present invention also includes variants of the aforementioned sequences, that is nucleotide sequences that vary from the reference sequence by conservative nucleotide substitutions, whereby one or more nucleotides are substituted by another with same characteristics.

Yet another concern of the present invention is to provide an expression vector comprising the purified and isolated sequence encoding the chimeric inhibitor protein of a protease as described above. The choice of an expression vector depends directly, as it is well known in the art, on the functional properties desired, e.g., chimeric inhibitor protein expression and the host cell to be transformed or transfected.

Additionally, the expression vector may further comprise a promoter operably linked to the purified and isolated DNA sequence. This means that the linked isolated and purified DNA sequence encoding the chimeric inhibitor protein of a protease of the present invention is under control of a suitable regulatory sequence which allows expression, i.e. transcription and translation of the inserted isolated and purified DNA sequence.

As used herein, the term "promoter" designates any additional regulatory sequences as known in the art e.g. a promoter and/or an enhancer, polyadenylation sites and splice junctions usually employed for the expression of the polypeptide or may include additionally one or more separate targeting sequences and may optionally encode a selectable marker. Promoters which can be used provided that such promoters are compatible with the host cell are e.g promoters obtained from the genomes of viruses such as polyoma virus, adenovirus (such as Adenovirus 2), papilloma virus (such as bovine papilloma virus), avian sarcoma virus, cytomegalovirus (such as murine or human cytomegalovirus immediate early promoter), a retrovirus, hepatitis-B virus, and Simian Virus 40 (such as SV 40 early and late promoters) or promoters obtained from heterologous mammalian promoters, such as the actin promoter or an immunoglobulin promoter or heat shock promoters.

Enhancers which can be used are e.g. enhancer sequences known from mammalian genes (globin, elastase, albumin, a-fetoprotein, and insulin) or enhancer from a eukaryotic cell virus. e.g. the SV40 enhancer, the cytomegalovirus early promoter enhancer, the polyoma, and adenovirus enhancers.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAs, e.g., the numerous derivatives of phage X, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Most preferably the expression vector is pQE-9.

Another concern of the present invention is to provide a eukaryotic or prokaryotic host cell transformed or transfected with an expression vector described herein.

The term "cell transfected" or "cell transformed" or "transfected/transformed cell" means the cell into which the extracellular DNA has been introduced and thus harbours the extracellular DNA. The DNA might be introduced into the cell so that the nucleic acid is replicable either as a chromosomal integrant or as an extra chromosomal element.

Transformation or transfection of appropriate eukaryotic or prokaryotic host cells with an expression vector comprising a purified an isolated DNA sequence according to the invention is accomplished by well known methods that typically depend on the type of vector used. With regard to these methods, see for example, Maniatis et al. 1982, Molecular Cloning, A laboratory Manual, Cold Spring Harbor Laboratory and commercially available methods.

The chimeric inhibitor proteins disclosed herein are preferably produced, recombinantly, in a cell expression system.

A wide variety of unicellular host cells are useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture. Preferably, the host cell is a bacterial cell, more preferably an *E. coli* cell.

The present invention is also directed to a pharmaceutical composition comprising the chimeric inhibitor protein as described herein as an active agent, optionally in combination with one or more pharmaceutically acceptable carriers.

Preferably, in addition to at least one chimeric inhibitor protein as described herein, the pharmaceutical composition may contain one or more pharmaceutically acceptable carriers, such as excipients, carriers and/or auxiliaries which facilitates processing of the active compounds into preparation which can be used pharmaceutically.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The form of administration of the pharmaceutical composition may be systemic or topical. For example, administration of such a composition may be various parenteral routes such as subcutaneous, intravenous, intradermal, intramuscular, intraperitoneal, intranasal, transdermal, buccal routes or via an implanted device, and may also be delivered by peristaltic means.

The pharmaceutical composition comprising a chimeric inhibitor protein, as described herein, as an active agent may also be incorporated or impregnated into a bioabsorbable matrix, with the matrix being administered in the form of a suspension of matrix, a gel or a solid support. In addition the matrix may be comprised of a biopolymer.

Sustained-release preparations may be prepared. Suitable examples of sustained-release preparations include semi permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma]ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished for example by filtration through sterile filtration membranes.

It is understood that the suitable dosage of a chimeric inhibitor protein of the present invention will be dependent upon the age, sex, health, and weight of the recipient, kind of concurrent treatment, if any and the nature of the effect desired.

The appropriate dosage form will depend on the disease, the chimeric inhibitor protein, and the mode of administration; possibilities include tablets, capsules, lozenges, dental pastes, suppositories, inhalants, solutions, ointments and parenteral depots.

Since amino acid modifications of the amino acids of the chimeric inhibitor protein are also encompassed in the present invention, this may be useful for cross-linking the chimeric inhibitor protein to a water-insoluble matrix or the other macromolecular carriers, or to improve the solubility, adsorption, and permeability across the blood brain barrier. Such modifications are well known in the art and may alternatively eliminate or attenuate any possible undesirable side effect of the protein and the like.

While a preferred pharmaceutical composition of the present invention comprises a chimeric inhibitor protein as an active agent, an alternative pharmaceutical composition may contain a purified and isolated DNA sequence encoding the chimeric inhibitor protein of a protease, as described herein, as an active agent. This pharmaceutical composition may include either the sole purified and isolated DNA sequence, an expression vector comprising said purified and isolated DNA sequence or a host cell previously transfected with an expression vector described herein. In this latter example, host cell will preferably be isolated from the patient to be treated in order to avoid any antigenicity problem. These gene and cell therapy approaches are especially well suited for patients requiring repeated administration of the pharmaceutical composition, since the said purified and isolated DNA sequence, expression vector or host cell previously transfected with an expression vector can be incorporated into the patient's cell which will then produce the protein endogenously.

The present disclosure also provides a method of treating or preventing a proteolysis-associated disorder in a mammal comprising administering to said mammal the pharmaceutical composition as described herein.

The present method of treating or preventing a proteolysis-associated disorder can be useful in case the disorder is a disorder in which hK2 kallikrein activity is detrimental such as a cancer, an autoimmune disorder, an inflammatory disorder such as Benign Prostatic Hypertrophy, or an infectious disorder.

The term "cancer" refers to or describes the physiological condition in mammals that is typically characterized by unregulated cell growth. Examples of cancers, which can be treated, include but are not limited to prostate cancer, breast cancer or a metastasic cancer.

In preferred methods, the mammal is a human patient, and the administered chimeric inhibitor protein is selected from the recombinant serpin examples of Table III, which specifically inhibits the hK2 protease.

Embraced by the scope of the present invention is also the use of the pharmaceutical composition described herein for the preparation of a medicament for the treatment or prevention of a proteolysis-associated disorder in a mammal in case the disorder is a disorder in which hK2 kallikrein activity is detrimental such as a cancer, an autoimmune disorder, an inflammatory disorder such as Benign Prostatic Hypertrophy, or an infectious disorder.

Examples of cancers include but are not limited to prostate cancer, breast cancer or a metastasic cancer.

The chimeric inhibitor proteins of the invention will generally be used in an amount to achieve the intended purpose. For use to treat or prevent a disorder, the chimeric inhibitor proteins or the pharmaceutical compositions thereof, are administered or applied in a therapeutically effective amount. A "therapeutically effective amount" is an amount effective to ameliorate or prevent the symptoms, or prolong the survival of, the subject being treated. Determination of a therapeutically effective amount is well within the capabilities of those skilled in the art, especially in light of the detailed disclosure provided herein.

For systemic administration, a therapeutically effective amount or dose can be estimated initially from in vitro assays. For example, a dose can be formulated in animal models to achieve a circulating concentration range that includes the IC50 as determined in cell culture. Such information can be used to more accurately determine useful doses in humans.

Initial doses can also be estimated from in vivo data, e.g. animal models, using techniques that are well known in the art. One ordinarily skill in the art could readily optimise administration to humans based on animal data and will, of course, depend on the subject being treated, on the subject's weight, the severity of the disorder, the manner of administration and the judgement of the prescribing physician.

The present invention also encompasses a method for producing a chimeric inhibitor protein of a protease, said method comprising the steps of
a) selecting a polynucleotidic sequence encoding a substrate-enzyme interaction site specific for a protease,
b) introducing said polynucleotidic sequence into a sequence encoding an inhibitor protein of a serine or cysteine protease, so as to obtain a chimeric sequence,
c) allowing expression of said chimeric sequence in a cell expression system under suitable conditions,
d) and recovering the chimeric inhibitor protein of a protease.

Selecting a polynucleotidic sequence encoding a substrate active site specific for a protease can be done by the following different techniques such as, for example, displaying substrates for protease selection such as a murine leukemia retrovirus displaying a peptide directly from living cells thus avoiding passage in bacteria (Buchholz et al., 1998) or a similar method using chimeric Sindbis virus libraries which was also employed for the in vivo selection of protease cleavage sites using mammalian cells transfected with the enzyme of interest (Pacini et al, 2000 "In vivo selection of protease cleavage sites by using chimeric Sindbis virus libraries" *J. Virol.* 74, 22: 10563-70).

Also envisioned is a yeast system, GASP (genetic assay for site specific proteolysis) which consists in fusing random substrates to an integral membrane protein, allowing the attachment of the substrate to the membrane yeast, where cytoplasmic transcription factors can bind to promoter of a reporter gene (Kang et al., 2001 "An improved strategy for a genetic assay for site-specific proteolysis" *Mol. Cell.* 30; 11(2): 263-6).

Recently have emerged a number of combinatorial chemical libraries for determining protease substrate specificity. These include combinatorial fluorogenic substrate libraries and positional scanning-synthetic combinatorial libraries.

Another method, named immobilized peptide library, allows determination of relative substrate specificity (kcat/Km) for each member of the library by measuring fluorescence intensity in the solution phase and to identify the scissile bond by Edman sequencing (Hu et al. 2002 "Rapid determination of substrate specificity of *clostridium histolyticum* beta-collagenase using an immobilized peptide library" *J. Biol. Chem.* 8, 277 (10):8366-71).

In case substrate specificity of a protease is determined by phase display technology, a phage-displayed random peptide library with exhaustive diversity is generated and screened with purified protease. This known technique has been adapted to the specific case as described herein in order to construct a phage-displayed random library that included all possible amino acid combination of a defined length of amino acids. Thus large libraries are constructed by displaying random sequences on the extremity of filamentous phages, then amplified and screened toward a protease to assay rapidly its specificity.

According to Examples 1 and 2, Applicants have constructed a pentamer library containing $1.8 \times 10^8$ independent transformants which could then be considered complete because, in theory all of the $3.2 \times 10^6$ possible random pentamer sequences were represented. The sequences of phages further confirmed the randomness of the pentamer inserts. Then phage displaying the random pentapeptides are fused to a ligand (6×His) and are immobilized on an affinity support, in this case Ni-NTA matrix. Following incubation with the protease, (in the case of examples 1 and 2 the protease was hK2) phages expressing sensitive substrates are released from the solid phase. The released phages are used to infect F-positive bacteria to be titrated and amplified. These phages are then purified by precipitation, amplified and then immobilized to affinity support to proceed for a next round of selection. This selection of pentapeptides has been repeated 8 times in total in order to obtain high specific polynucleotidic sequence. Phages from the last round are cloned by plating onto Petri dishes and DNA of individual phages is amplified in region encoding a substrate active site to determine the sequences cleaved by the enzyme.

Polynucleotidic sequences encoding a substrate active site are then introduced into a sequence encoding an inhibitor of a serine protease, for example into a sequence encoding rACT, so as to obtain a chimeric sequence. Two silent restriction sites Sac II and Mlu I previously incorporated 18 bp upstream and 18 bp downstream of P1 codon in RSL domain of rACT allowed the subcloning of the selected polynucleotidic sequence encoding a substrate active site.

Recombinant chimeric inhibitors are, for example, produced in TG1 *E. coli* strains at suitable culturing conditions. Suitable culturing conditions can be comprised between 10-40° C. during 10-30 hours depending on the recombinant chimeric inhibitors to be expressed. Surprisingly, Applicants have shown that in the case of examples 1 and 2, a temperature of 16° C. during 16 h allows the expression and the production of fully intact variants of rACTs.

Finally, recombinant chimeric inhibitors can be recovered either from the culturing medium, when the recombinant chimeric inhibitor is secreted, or extracted from the cell expression system when the recombinant chimeric inhibitor is not secreted, and purified by art-known techniques such as high performance liquid chromatography, gel electrophoresis, affinity chromatography, ultrafiltration, ion exchange and the like. The actual conditions used to purify a particular recombinant chimeric inhibitor will depend, in part, on factors such as net charge, hydrophobicity, hydrophilicity, etc. and will be apparent to those skilled in the art.

For affinity chromatography purification, any antibody which specifically binds to the recombinant chimeric inhibitor or to the His tag may be used. Other affinity molecules such as $Ni^{2+}$-nitrilotriacetic linked to agarose beads and which bind specifically to the His tag are also envisioned in the present invention.

The chimeric inhibitor proteins may then further be assayed for their ability to inhibit the activity of the protease. This can be done by any conventional method such as the Scatchard method (Scatchard, 1949 *Ann NY Acad Sci* 51: 660-669). This method describes a classical method of measuring and analysing binding which has been applied to the binding of proteins and requires relatively pure protein and the ability to distinguish bound protein from unbound.

A second method appropriate for measuring the affinity of chimeric inhibitor proteins for enzymes is to measure the ability of the chimeric inhibitor proteins to slow the action of the enzyme. This method requires, depending on the speed at which the enzyme cleaves substrates and the availability of chromogenic or fluorogenic substrates relatively pure chimeric inhibitor proteins.

Preferably, the chimeric inhibitor proteins of the present invention inhibit the protease activity with a higher affinity than their wild type counterparts.

The chimeric inhibitor proteins disclosed herein are preferably produced, recombinantly, in a cell expression system. This system can be a eukaryotic or a prokaryotic host cell.

A wide variety of unicellular host cells are useful in expressing the chimeric inhibitor proteins of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture. Preferably, the host cell is a bacterial cell selected from the group comprising the genera *Bacillus, Escherichia, Salmonella*, and *Erwinia*. More preferably the bacterial host cell is an *E. coli* cell.

Transformation or transfection of appropriate eukaryotic or prokaryotic host cells with an expression vector comprising a purified an isolated DNA sequence according to the invention is accomplished by well known methods that typically depend on the type of vector used. With regard to these methods, see for example, Maniatis et al. 1982, Molecular Cloning, A laboratory Manual, Cold Spring Harbor Laboratory and commercially available methods.

A further object of the present invention is to provide an diagnostic kit for the detection of a protease, in vivo or in vitro, in a specimen comprising a purified and isolated DNA sequence selected from the group comprising SEQ ID No 1, 3, 5, 7, 9, 11, 13, a sequence complementary thereof, fragments thereof, and/or variants thereof.

Alternatively, the present invention also envisioned a diagnostic kit for the detection of a protease in a specimen comprising a chimeric inhibitor protein of a protease according to the present invention. Said chimeric inhibitor protein of a protease may, for example, be selected from the group comprising MD820, MD 62, MD 61, MD67 and MD CI.

As used herein, the term "specimen" refers to any suitable sample that may contain a protease, or a sequence encoding for a protease, to which may bind the chimeric inhibitor protein or the purified an isolated DNA sequence encoding for said chimeric inhibitor protein.

The diagnostic kit may include a system enabling the detection of a protease wherein detection of the signal will depend on the amount of protease present. The signal may be detected visually or instrumentally. Possible signals may include production of coloured, fluorescent, or luminescent products, alteration of the characteristics of absorption or emission of radiation by an assay component or product, and precipitation or agglutination of a component product. Said component may be a label, e.g. a radioisotope, a fluorophore, an enzyme, a co-enzyme, an enzyme substrate, an electron-dense compound, or an agglutinable particle and may be coupled either to the chimeric inhibitor protein or to the purified and isolated DNA sequence present in this diagnostic kit.

Finally, the present disclosure also provides a method of treating or preventing a proteolysis-associated disorder in a mammal comprising administering to said mammal a pharmaceutical composition comprising a recombinant wild type serpin as an active agent.

The aforementioned method of treating or preventing a proteolysis-associated disorder can be useful in case the disorder is a disorder in which hK2 kallikrein activity is detrimental such as a cancer, an autoimmune disorder, an inflammatory disorder such as Benign Prostatic Hypertrophy, or an infectious disorder.

The foregoing description will be more fully understood with reference to the following Examples. Such Examples, are, however, exemplary of methods of practising the present invention and are not intended to limit the scope of the invention.

EXAMPLES

Example 1

Development of Recombinant ACT Inhibitors Specific to Human hK2 Using Phage Display Selected Substrates Material hK2 and hK3 (PSA) were purified from human semen as previously described (Frenette G, Gervais Y, Tremblay R R, Dube J Y. 1998 "Contamination of purified prostate-specific antigen preparations by kallikrein hK2" *J Urol* 159, 1375-8), anti-hK2 and anti-PSA monoclonal antibodies were a gift from Professor R R Tremblay, Laval University, Canada. Human chymotrypsin (Chtr), urokinase plasminogen activator (uPA), human kallikrein hK1, human plasma kallikrein (PK), human neutrophil elastase (HNE) and commercial ACT (human plasma α1-antichymotrypsin) were purchased from Calbiochem. Z-Phe-Arg-AMC, Suc-Ala-Ala-Pro-Phe-AMC (SEQ ID NO: 103), Z-Gly-Gly-Arg-AMC, MeOSuc-Ala-Ala-Pro-Val-AMC (SEQ ID NO: 104) were purchased from Calbiochem. CFP-TFRSA-YFP (SEQ ID NO: 130) fluorescent substrate was developed as previously described (Mahajan N P et al. 1999 "Novel mutant green fluorescent protein protease substrates reveal the activation of specific caspases during apoptosis" *Chem Biol* 6, 401-9). The cDNA for human α1-antichymotrypsin (ACT) was a generous gift from Dr. Harvey Rubin (University of Pennsylvania).

Site-Directed Mutagenesis

Figure 9:
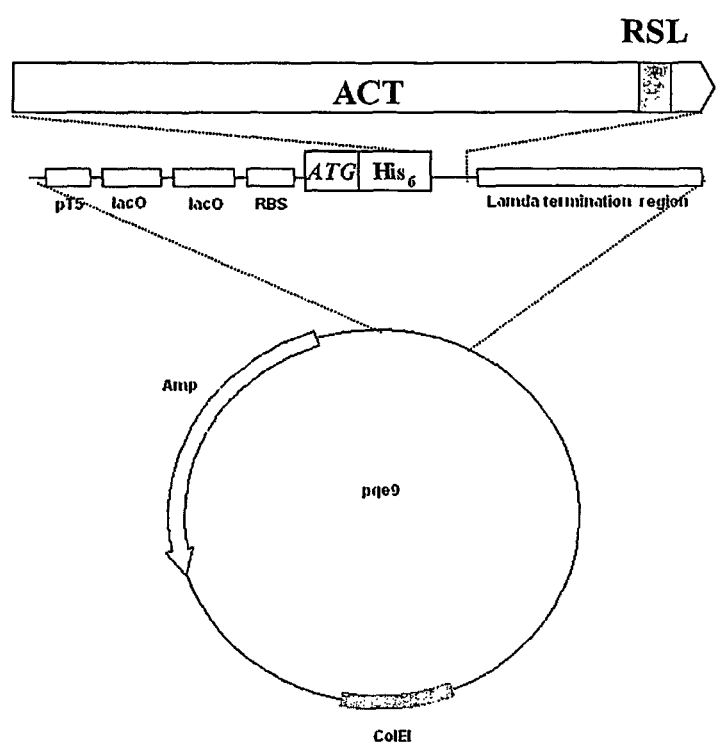
FIG. 9 represents the pQE9 expression vector map.

Following the subcloning of ACT cDNA into pQE-9 expression vector (Qiagen, Germany, FIG. 9) and the introduction of an $His_6$ tag at the N-terminal of $rACT_{WT}$, two restriction sites Sac II and MluI, were incorporated 18 by upstream and 18 by downstream of P1 codon in RSL domain respectively. These sites were created by silent mutation using oligonucleotides 5'-GTGATTTTGACCGCGGTG-GCAGCAG-3' (SEQ ID NO: 105) for Sac II and 5'-GCA-CAATGGTACGCGTC TCCACTAATG-3' (SEQ ID NO: 106) for Mlu I site and following the quickchange mutagenesis protocol supplied by Stratagene.

Construction of the Substrate Phage Display Library

Substrate phage libraries were generated using a modified pH0508b phagemid (Lowman et al. 1991 "Selecting high-affinity binding proteins by monovalent phage display" *Biochemistry* 12, 10832-8). The construction consists of a $His_6$ tag at either end of a Gly-Gly-Gly-Ser- (SEQ ID NO: 107) repeat-rich region that precedes the carboxyl-terminal domain (codons 249-406) of the M13 gene III. The random pentamers were generated by PCR extension of the template oligonucleotides with appropriate restriction sites positioned on both side of the degenerate codons: 5'TGAGCTAGTCTA-GATAGGTGGCGGTNNSNNSNNSNNSNNSGGGTCGACGTCGGTCATAGCAGTCGCTGCA-3' (SEQ ID NO: 108) (where N is any nucleotide and S is either G or C) using 5' biotinylated primers corresponding to the flanking regions: 5'TGAGCTAGTCTAGATAGGTG-3' (SEQ ID NO: 109) and 5'-TGCAGCGACTGCTATGA-3'. (SEQ ID NO: 110).

PCR templates are digested and purified as described previously (Smith G. P, Scott J. K. 1993 "Libraries of peptides and proteins displayed on filamentous phage" *Methods Enzymol.* 217, 228-57), inserted into XbaI/SalI digested pH0508b vector, and electroporated into XL1-Blue (F⁻). The extent of the library was estimated from the transformation efficiency determined by plating a small portion of the transformed cells onto Luria-Bertani plates containing ampicillin and tetracycline (100 and 15 µg·mL⁻¹, respectively). The rest of the transformed cells were used to prepare a phage library by incubating overnight by adding an M13K07 helper phage at a concentration giving a multiplicity of infection of 100 plaque forming units (p.f.u.) per mL. Phages were collected from the supernatant and purified by poly(ethylene glycol) precipitation. Of these, 200 clones were selected arbitrarily for sequencing to verify the randomization of the library.

Phage-Displayed Pentapeptide Library Screening

This new pentapeptide library was subjected to eight rounds of screening with hK2. One hundred microliters of $Ni^{2+}$-nitrilotriacetic acid coupled to sepharose beads ($Ni^{2+}$-nitrilotriacetic acid resin) was washed with 10 mL NaCl/$P_i$ containing 1 mg·mL⁻¹ BSA. Phage particles ($10^{11}$) were added to the equilibrated $Ni^{2+}$-nitrilotriacetic acid resin and allowed to bind with gentle agitation for 3 h at 4° C. The resin was subsequently washed (NaCl/$P_i$/BSA 1 mg·mL⁻¹, 5 mM imidazole, 0.1% Tween 20) to remove unbound phages and then equilibrated in NaCl/Pi. The substrate phage was exposed to 27 nm (final concentration) of hK2 for 45 min at 37° C. A control selection without protease was also performed. The cleaved phages released into the supernatant were amplified using XL1-Blue *Escherichia coli* and then used for subsequent rounds of selection. After eight rounds of panning, about 15 individual clones were picked from the fifth, sixth and eighth round of selection and plasmid DNA were isolated and sequenced in the region encoding for the substrate.

Construction and Expression of Recombinant Wild Type ACT and its Variants.

Six variants, which correspond to a change in the reactive site loop in positions between P3 and P3' (see Table IV below), were generated by PCR extension of the template oligonucleotides:

(SEQ ID NO: 111)
$rACT_{8.20}$, 5'-TACCGCGGTCAAAATCACCCTCCGTTCTCAGCAGTGGAGACGCGT GA-3';

(SEQ ID NO: 112)
$rACT_{6.3}$, 5'-TACCGCGGTCAAAATCACCAGGAGGTCTATCGATGTGGAGACGCGTGA-3';

(SEQ ID NO: 113)
$rACT_{8.3}$, 5'-TACCGCGGTCAAAATCAGGGGGAGATCTGAGTTAGTGGAGACGCGTGA-3';

(SEQ ID NO: 114)
$rACT_{6.7}$, 5'-TACCGCGGTCAAAATCAAGCTTAGAACAACATTAGTGGAGACCGCTGA-3';

(SEQ ID NO: 115)
$rACT_{6.1}$, 5'-TACCGCGGTCAAAATCATGACAAGATCTAACTTAGTGGAGACGCGTGA-3';

(SEQ ID NO: 116)
$rACT_{5.18}$, 5'-TACCGCGGTCAAAATCACCGAGCGTGTCTCGCCCGTGGAGACGCGTGA-3'

(where underlined sequences encode new cleavage sites in the reactive site loop), using primers corresponding to the flanking regions: 5'-TACCGCGGTCAAAATC-3' (SEQ ID NO: 117) and 5'-TCACGCGTGTCCAC-3' (SEQ ID NO: 118). PCR products were digested with Sac II and Mlu I restriction enzymes and then subcloned into digested $rACT_{WT}$ construct. Recombinant serpins were produced in TG1 *E. coli* strain. Cells were grown at 37° C. in 2×TY media (16 g tryptone, 10 g yeast extract, 5 g NaCl per L) containing 100 µg/ml ampicillin to $A_{600}$=0.5. Isopropylthio-β-galactoside (IPTG) was then added to a final concentration of 0.5 mM allowing the expression of recombinant serpins for 16 h at 16° C. The cells from 100 ml of culture were harvested by centrifugation, resuspended in cold PBS and then passed through a french press to recover the total soluble cytoplasmic proteins. Cell debris were removed by centrifugation and $Ni^{2+}$-nitilotriacetic affinity agarose beads were added to supernatant for 90 min at 4° C. to bind recombinant serpins. The resin was subsequently washed with 50 mM Tris pH 8.0, 500 mM NaCl, 25 mM Imidazole and the bound proteins were eluted for 10 min with 50 mM Tris pH 8.0, 500 mM NaCl and 150 mM Imidazole. Once purification was completed, rACT were dialysed against 50 mM Tris pH 8.0, 500 mM NaCl, 0.05% Triton X-100 for 16 h at 4° C. The protein concentration was determined for each purification by Bradford assay and normalized by densitometry of Coomassie Blue-stained SDS-PAGE gels (Laemmli U K. 1970 "Cleavage of structural proteins during the assembly of the head of bacteriophage T4" *Nature* 227, 680-5).

TABLE IV

Alignment of RSL (Reactive Serpin Loop) of recombinant serpin α1-antichymotrypsin (ACT) and its variants.

| Serpin | Selected[a] Substrate Peptide | P6 | P5 | P4 | P3 | P2 | P1 | P'1 | P'2 | P'3 | P'4 | P'5 | P'6 | SEQ NO |
|---|---|---|---|---|---|---|---|---|---|---|---|---|---|---|
| $rACT_{WT}$ | | V | K | I | T | L | L* | S | A | L | V | E | T | 119 |
| $rACT_{8.20}$ | LR↓SRA | V | K | I | T | L | R* | S | R | A | V | E | T | 120 |
| $rACT_{6.2}$ | RR↓SID | V | K | I | T | R | R* | S | I | D | V | E | T | 121 |

TABLE IV-continued

Alignment of RSL (Reactive Serpin Loop) of recombinant serpin α1-antichymotrypsin (ACT) and its variants.

| Serpin | Selected[a] Substrate Peptide | P6 | P5 | P4 | P3 | P2 | P1 | P'1 | P'2 | P'3 | P'4 | P'5 | P'6 | SEQ NO |
|---|---|---|---|---|---|---|---|---|---|---|---|---|---|---|
| rACT$_{8.3}$ | RGR↓SE | V | K | I | R | G | R* | S | E | L | V | E | T | 122 |
| rACT$_{6.7}$ | KLR↓TT | V | K | I | K | L | R* | T | T | L | V | E | T | 123 |
| rACT$_{6.1}$ | MTR↓SN | V | K | I | M | T | R* | S | N | A | V | E | T | 124 |
| ACT$_{5.18}$ | ER↓VSP | V | K | I | T | E | R* | V | S | P | V | E | T | 125 |

[a]Substrate peptides selected by kallikrein hK2 using a phage-displayed random pentapeptide library. Plain type residues are common to rACT$_{WT}$, bold and underlined residues correspond to substrate peptides relocated in RSL of ACT variants. The scissile bond by hK2 in substrate peptides is designated by ↓ and putative cleavage site in serpins is marked by asterisks between the P1-P1' residues.

Inhibition Assays and Stoichiometry of Inhibition (SI)

The stoichiometry of inhibition (SI) values were determined for the inhibition of rACT$_{WT}$ and its variants with hK2 and different other enzymes. An initial test was made with a molar excess of rACT (100 fold) over hK2, PSA, hK1, chymotrypsin (Chtr), plasma kallikrein (PK), urokinase (uPA) and human neutrophile elastase (HNE) enzymes. The reaction was carried out for 30 min at 25° C. (90 min at 37° C. for PSA) in reaction buffer (50 mM Tris pH 7.5, 150 mM NaCl, 0.05% Triton X-100, 0.01% BSA) and residual enzyme activity was measured by adding fluorescent substrates (Z-Phe-Arg-AMC for hK1, hK2 and PK, Suc-Ala-Ala-Pro-Phe-AMC for Chtr, Z-Gly-Gly-Arg-AMC for uPA, MeOSuc-Ala-Ala-Pro-Val-AMC for HNE, and CFP-TFRSA-YFP for PSA). Activity of enzyme in presence of inhibitors was compared to uninhibited reaction. For reactions where an inhibition was observed, SI was determined by incubating different concentrations of recombinant serpins. Using linear regression analysis of fractional activity (velocity of inhibited enzyme reaction/velocity of uninhibited enzyme reaction) versus the molar ratio of the inhibitor to enzyme ($[I_o]/[E_o]$), the stoichiometry of inhibition, corresponding to the abscissa intercept, was obtained.

Kinetics

The association rate constants for interactions of hK2, chymotrypsin, PK and HNE with different rACTs were determined under pseudo-first order conditions using the progress curve method (Morrison J F, Walsh C T. 1988 "The behavior and significance of slow-binding enzyme inhibitors" *Adv. Enzymol. Relat. Areas Mol. Biol* 61, 201-301). Under these conditions, a fixed amount of enzyme (2 nM) was mixed with different concentrations of inhibitor (0-800 nM) and an excess of substrate (10 μM). Each reaction was made in reaction buffer (50 mM Tris pH 7.5, 150 mM NaCl, 0.05% Triton X-100, 0.01% BSA) at 25° C. for 45 min and the rate of product formation was measured using a FL$_x$800 fluorescence 96-well microplate reader (Biotek, USA). In this model, inhibition is considered to be irreversible over the course of reaction and the progress of enzyme activity is expressed by product formation (P), beginning at a rate ($v_z$) and is inhibited over time (t) at a first-order rate ($k_{obs}$), rate constant that is dependent only on inhibitor concentration.

$$P=(v_z/k_{obs}) \times [1-e^{(-k_{obs}t)}] \qquad \text{eq 1}$$

For each inhibitor, a $k_{obs}$ was calculated, for four different concentrations of inhibitors, by non linear regression of the data using equation 1. By plotting the $k_{obs}$ versus inhibitor concentration [I], a second-order rate constant, k', equal to the slope of the curve (k'=Δ$k_{obs}$/Δ[I]), was determined. Due to the competition between inhibitor and the substrate, equation 2 below is used to correct the second order rate constant k' by taking in account the substrate concentration [S] and the $K_m$ of the enzyme for its substrate, giving the k.

$$k_a=(1+[S]/K_m) \times k' \qquad \text{eq2}$$

The $K_m$ of hK2 for Z-FR-AMC, chymotrypsin for Suc-AAPF-AMC, PK for Z-FR-AMC and HNE for MeOSuc-AAPV-AMC were 67 μM, 145 μM, 170 μM and 130 μM respectively.

Western Blot Analysis of Complex Formation and Inhibitor Degradation.

Kallikrein hK2 was incubated 3 hours at 37° C. with different recombinant ACTs at a $[I]_o:[E]_o$ ratio of 100:1 in 50 mM Tris, 200 mM NaCl, 0.05% Triton X-100. Protein samples were heated at 95° C. for 5 min, separated by SDS-PAGE (12% acrylamid 19:1 T:C ratio) and then electroblotted onto Hybond-ECL (Amersham Pharmacia) nitrocellulose. The free-hK2 and hK2-ACT complexes were detected using a mouse anti-hK2 monoclonal antibody and an alkaline phosphatase-conjugated goat anti-mouse secondary antibody. Western blot was visualized using the ECL detection kit (Amersham Pharmacia Biotech). hK2 was also incubated with ACT$_{8.3}$ or ACT$_{6.7}$ 30 min at 25° C. (kinetic conditions) at a $[I_o]:[E]_o$ ratio of 10:1 in 50 mM Tris, 200 mM NaCl, 0.05% Triton X-100. Proteins were detected by western blot, using an anti-His$_6$ monoclonal antibody followed by detection with the secondary antibody and protocol described above.

Production of Soluble Recombinant Wild Type and Variant ACTs

Wild type serpin α1-antichymotrypsin was used to develop specific inhibitors of the kallikrein hK2. Residues P3-P3' located in RSL structure of rACT$_{WT}$ were replaced by substrate pentapeptides, previously selected by phage display technology as described above. Six variants of rACT shown in table I, have been designed and constructed. The scissile bond in substrate peptides was aligned according to Leu-358-Ser-359 into RSL of the serpin. rACT$_{WT}$ and its variants were expressed in *E. coli* TG1 as fusion proteins containing an His tag in N-terminal position. Each of them was produced at low temperature allowing protein accumulation mainly in active soluble form. Purified under native conditions, the level of production varied between 1.0 to 2.5 mg/L. The purity of purified serpins, such as for example Variant 6.1 (lane 1) and wild type ACT (lane 2), as estimated by SDS-PAGE analysis is more than 98% (FIG. 1).

rACT Variants are Mainly Specific to Kallikrein hK2

A panel of enzymes including human neutrophil elastase, chymotrypsin-like (Chtr, PSA or hK3) and trypsin-like (hK2, hK1, PK, uPA) proteinases have been screened to determine inhibitory specificity of rACT variants (Table V).

TABLE V

Inhibitory profile of rACT$_{WT}$ and its variants.

| Protease | ACT$_{8.20}$ (LR↓SRA)[a] MD820 | ACT$_{6.2}$ (RR↓SID)[a] MD62 | ACT$_{8.3}$ (RGR↓SE)[a] MD83 | ACT$_{6.7}$ (KLR↓TT)[a] MD67 | ACT$_{6.1}$ (MTR↓SN)[a] MD61 | ACT$_{5.18}$ (ER↓VSP)[a] MD518 | ACT$_{WT}$ (LL↓SA)[a] |
|---|---|---|---|---|---|---|---|
| | | | | Inhibition %[b] | | | |
| hK2 | 95 | 100 | 100 | 100 | 100 | 73 | 0 |
| Chtr | 66 | 0 | 0 | 0 | 0 | 0 | 100 |
| PK | 54 | 100 | 0 | 36 | 100 | 0 | 0 |
| HNE | 30 | 0 | 0 | 0 | 60 | 0 | 15 |
| PSA (hK3) | 45 | 0 | 0 | 0 | 0 | 0 | 80 |
| hK1 | 0 | 0 | 0 | 0 | 0 | 0 | 0 |
| Urokinase | 0 | 0 | 0 | 0 | 0 | 0 | 0 |

[a]Amino acid sequence cleaved in RSL (Reactive Serpin Loop) of recombinant ACTs corresponding to selected substrate peptide by hK2.
[b]Protease and serpins were incubated for 30 min at 25° C. (90 min at 37° for PSA) at a [I]$_o$/[E]$_o$ ratio of 100:1. Percent inhibition correspond to 100 × (1 − (velocity in presence of inhibitor/velocity of uninhibited control)).

Incubating with an excess of inhibitors ([I]$_o$/[E]$_o$ of 100:1) for 30 minutes, hK2 is completely inhibited by rACT$_{6.2}$, rACT$_{8.3}$, rACT$_{6.7}$ and rACT$_{6.1}$, whereas rACT$_{8.20}$ and rACT$_{5.18}$ inhibited 95% and 73% of enzyme activity, respectively. Under this condition, wild type rACT showed no inhibition activity toward hK2. Among these variants, two (rACT$_{8.3}$ and rACT$_{5.18}$) are specific to hK2, inhibiting no other tested enzyme. Two other variants, rACT$_{6.7}$ and rACT$_{6.2}$, inhibited as well PK at 36% and 100% respectively. As wild-type ACT, variant rACT$_{8.20}$ inhibited the two chymotrypsin-like proteases Chtr and PSA but additionally also PK and HNE. None of the recombinant serpins showed inhibitory activity against the kallikrein hK1 and uPA.

Stoichiometries of Inhibitory of Variant ACTs for hK2 are Improved Drastically in Comparison to Wild Type ACT The determination of the stoichiometry of inhibitory was accomplished under physiological conditions of pH and ionic strength for all enzymes to ensure the most valuable comparison. Recombinant wild type ACT gave a SI value of 2 (table VI) with chymotypsin which is identical to the value obtained with commercial ACT under similar conditions (data not shown).

In order to determine the SI values of all the recombinant variants, Applicants have incubated hK2 (5 nM) with different concentrations (6.25-500 nM) of rACT$_{8.20}$ (x), rACT$_{6.2}$ (□), rACT$_{8.3}$ (Δ), rACT$_{6.7}$ (◇), rACT$_{6.1}$ (✳), rACT$_{5.18}$ (○), rACT$_{WT}$ (+), at 25° C. for 30 min in reaction buffer. Residual activities (velocity) for hK2, were assayed by adding the fluorescent substrate (10 μM) Z-FR-AMC. Fractional velocity corresponds to the ratio of the velocity of inhibited enzyme ($v_i$) to the velocity of the uninhibited control ($v_o$). The SI was determined using linear regression analysis to extrapolate the I/E ratio (i.e. the x intercept).

Figure 2:
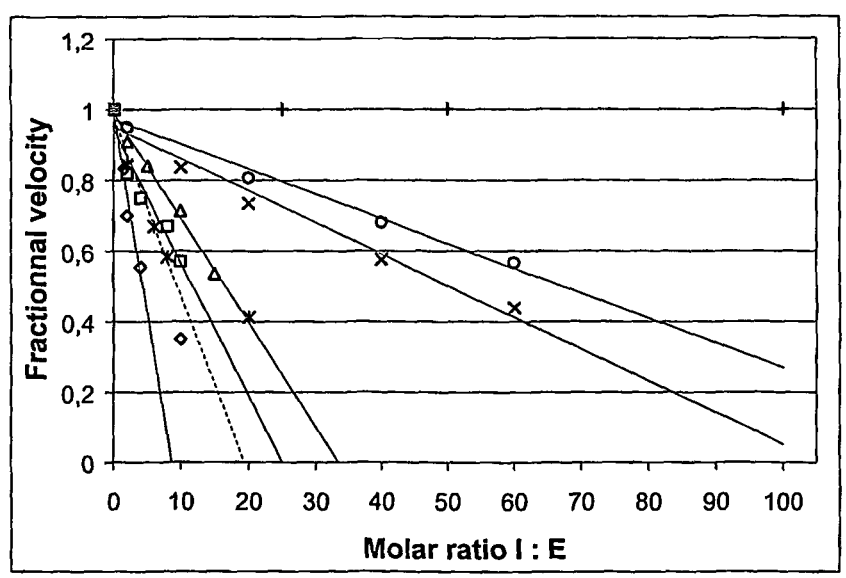
FIG. 2 shows the stoichiometry of inhibition (SI) of hk2 by $rACT_{WT}$ and its variants. The SI was determined using linear regression analysis to extrapolate the I/E ratio (i.e. the x intercept).

As shown in FIG. 2 all newly constructed variants of ACT showed lower SI values with hK2 than wild type ACT. From these variants rACT$_{6.7}$, rACT$_{6.1}$ and rACT$_{6.2}$ had the lowest stoichiometry of inhibition values for hK2 (9, 19 and 25 respectively). Whereas rACT$_{6.2}$ and rACT$_{6.1}$ had also the lowest SI values (18 and 16) for PK, the SI for rACT6.7 was much higher (277). The two recombinant ACTs specific for hK2, rACT$_{8.3}$ and rACT$_{5.18}$ had a higher SI ratio of 34 and 139, respectively. The SI value of rACT$_{8.20}$ inhibitor was superior to 100 for all tested proteases including hK2.

Variant ACTs Form Stable Complexes with hK2 without Degradation of Inhibitors hK2 was incubated 3 h at 37° C. with rACT$_{8.20}$, rACT$_{6.2}$, rACT$_{8.3}$, rACT$_{6.7}$, rACT$_{6.1}$, rACT$_{5.18}$ and wild type rACT, at a I:E ratio of 100:1. Western Blot analysis of the reaction products of rACTs with hK2 (rACT$_{8.20}$ (lane 1), rACT$_{6.2}$ (lane 2), rACT$_{8.3}$ (lane 3), rACT$_{6.7}$ (lane 4), rACT$_{6.1}$ (lane 5), rACT$_{5.18}$ (lane 6) and wild type rACT (lane 7)), has been done under reducing conditions using a mouse anti-hK2 antibody to determine the fate of inhibitors after the interaction with the enzyme. FIG. 3A shows that when hK2 is incubated with ACT variants, free hK2 (E) disappeared completely to form a covalent complex (EI). This covalent complex demonstrated a high stability as it did not break down over a 16 h incubation period (data not shown). Wild type ACT inhibited more

TABLE VI

Comparison of stoichiometry of inhibition values and second-order rate constants ($k_a$) for the reaction of rACT$_{WT}$ and its variants with hK2 and others proteinases.

| | ACT$_{8.20}$ (LR↓SRA)[c] MD820 | | ACT$_{6.2}$ (RR↓SID) MD62[c] | | ACT$_{8.3}$ (RGR↓SE) MD83[c] | | ACT$_{6.7}$ (KLR↓TT) MD67[c] | | ACT$_{6.1}$ (MTR↓SN) MD61[c] | | ACT$_{5.18}$ (ER↓VSP) MD518[c] | | ACT$_{WT}$ (LL↓SA)[c] | |
|---|---|---|---|---|---|---|---|---|---|---|---|---|---|---|
| Protease | SI | $(k_a)^b$ M$^{-1}$s$^{-1}$ | SI | $k_a^b$ M$^{-1}$s$^{-1}$ | SI | $k_a^b$ M$^{-1}$s$^{-1}$ | SI | $k_a^b$ M$^{-1}$s$^{-1}$ | SI | $k_a^b$ M$^{-1}$s$^{-1}$ | SI | $k_a^b$ M$^{-1}$s$^{-1}$ | SI | $k_a^b$ M$^{-1}$s$^{-1}$ |
| hK2 | 105 | 1779 | 25 | 6261 | 34 | 2439 | 9 | 8991 | 19 | 3442 | 139 | 595 | — | — |
| Chtr | 134 | 905 | — | — | — | — | — | — | — | — | — | — | 2 | 61295 |
| PK | 150 | 424 | 18 | 6217 | — | — | 277 | 201 | 16 | 8024 | — | — | — | — |
| HNE | 334 | 158 | — | — | — | — | — | — | 159 | 1192 | — | — | — | — |

[a]SI values reported were determined using linear regression analysis to extrapolate the I/E ratio (see FIG. 1).
[b]Second order rate constants for serpin-proteinase reactions were measured under pseudo-first- or second order conditions as described in "Experimental Procedure".
[c]Amino acid sequence of P3-P3' residues in RSL (Reactive Serpin Loop) of recombinant ACT corresponding to selected substrate peptide by hK2
—, No detectable inhibitory activity.

slowly hK2, which was mainly uncomplexed after 3 hours of incubation. Elevated SI values measured with hK2 were not due to non-complex forming degradation of ACT variant inhibitors.

Further on $ACT_{8.3}$ (lane 1) or $ACT_{6.7}$ (lane 3) were incubated with hK2 (lane 2 and 4 respectively on the western blot) under kinetic conditions (30 min at 25° C.) at a I:E ratio of 10:1. The complex formation was analysed by western blot under reducing conditions using a mouse monoclonal anti-his tag (FIG. 3B). All inhibitor proteins were either complexed with hK2 or present as uncleaved form, indicating that the possible substrate pathway for the serpin-enzyme interaction is marginal.

$1779\ M^{-1}s^{-1}$, for hK2, superior compared to Chtr, PK and HNE. One of the recombinant serpins, $rACT_{6.1}$, was reacting at higher velocity with PK than with hK2.

Example 2

Development of Recombinant ACT Inhibitors Specific to Human hK2 and hK3 Proteases Residues P3-P3' located in RSL structure of $rACT_{WT}$ were replaced by substrate pentapeptide coding for the RSL of Protein C Inhibitor (PCI) (Table VII) as described in example 1.

TABLE VII

Alignment of RSL (Reactive Serpin Loop) of recombinant serpins ACT, PCI and $ACT_{PCI}$.

| Serpin | | | P6 | P5 | P4 | P3 | P2 | P1 | P'1 | P'2 | P'3 | P'4 | P'5 | P'6 |
|---|---|---|---|---|---|---|---|---|---|---|---|---|---|---|
| $rACT_{WT}$ | Amino acid sequence | | V | K | I | T | L | L | S | A | L | V | E | T |
| | | | SEQ ID NO: 119 | | | | | | | | | | | |
| | DNA sequence (codon) | | GTC | AAA | ATC | ACC | CTC | CTT | TCT | GCA | TTA | GTG | GAG | GTC |
| | | | SEQ ID NO: 126 | | | | | | | | | | | |
| $rPCI_{WT}$ | Amino acid sequence | | T | I | F | T | F | R | S | A | R | L | N | S |
| | | | SEQ ID NO: 127 | | | | | | | | | | | |
| $rACT_{PCI}$ (MD CI) | Amino acid sequence | | V | K | I | T | F | R | S | A | L | V | E | T |
| | | | SEQ ID NO: 128 | | | | | | | | | | | |
| | DNA sequence (codon) | | GTC | AAA | ATG | ACC | TTT | *AGA* | TCT | GCA | TTA | GTG | GAG | GTC |
| | | | SEQ ID NO: 129 | | | | | | | | | | | |

Plain type residues are common to $rACT_{WT}$, bold and underlined residues correspond to substrate peptides relocated in RSL of ACT variants. The scissile bond in substrate peptides is designated by ↓ and putative cleavage site in serpins is marked by asterisks between the P1-P1' residues.

Variant ACTs Showed Highest Association Constants with hK2

The rate of inhibitory reaction with variant ACTs was determined for each protease showing reactivity with these inhibitors. To that end, interaction of hK2 and recombinant serpins was measured under pseudo-first order conditions using progress curve method. hK2 (2 nM) and substrate Z-FR-AMC (10 μM) were added to varying amounts (20 n-800 nM) of inhibitors $rACT_{8.20}$ (◇), $rACT_{5.18}$ (+) (FIG. 4A) and inhibitors $rACT_{6.2}$ (○), $rACT_{8.3}$ (□) $rACT_{6.7}$ (Δ), $rACT_{6.1}$ (x) (FIG. 4B). Representative progress curves were subjected to non linear regression analysis using eq 1 and the rate ($k_{obs}$) was plotted against the serpin concentrations. After determination of kobs, association constants (ka) were calculated using $K_m$ of the proteases for their corresponding substrates (table VI). The ka value of wild type ACT with chymotrypsin was identical as to published data (Cooley et al. 2001 "The serpin MNEI inhibits elastase-like and chymotrypsin-like serine proteases through efficient reactions at two active sites" Biochemistry 40, 15762-70). The recombinant $rACT_{6.7}$ showed a highest ka ($8991\ M^{-1}s^{-1}$) with hK2 whereas that obtained with PK was 45 fold inferior. In contrast, recombinant $rACT_{6.2}$ gave equivalent ka with hK2 and PK demonstrating a lack of discrimination between the two proteases. ka values of hK2 specific recombinant inhibitors $rACT_{8.3}$ and $rACT_{5.18}$ were lower, 2439 and 595 $M^{-1}s^{-1}$ respectively, whereas non specific $ACT_{8.20}$ exhibited a ka of Briefly, to produce the recombinant protein $ACT_{PCI}$ (MDCI), TG1 cells were transformed with the corresponding constructions followed by growth in appropriate culture media. Cells were then induced to an optimal density to express recombinant inhibitors for 16 h at 16° C. Recombinant inhibitor $ACT_{PCI}$ was extracted from cytoplasm bacteria and separated by affinity chromatography using Ni-NTA column as described for the previous example.

Analysis of Recombinant ACT Expression by SDS-PAGE.

Figure 5:
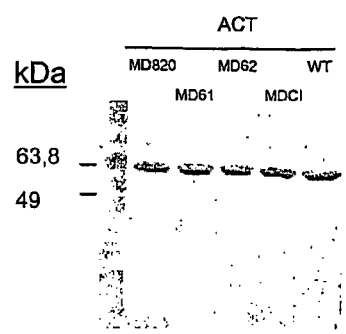
FIG. 5 corresponds to the determination of the purity of the inhibitors by SDS-PAGE analysis under reducing conditions of inhibitors developed in examples 1 and 2.

The purity of the different inhibitors developed in example 1 and 2 was tested by SDS-PAGE analysis under reducing conditions as shown in FIG. 5.

Evaluation of the Inhibitors.

These inhibitors were further analysed to assess their specificity and affinity to inhibit the human kallikreins hK2 and hK3 (FIG. 6) and plasma kallikrein, trypsin, urokinase, elastase, thrombin, hK14 and human kallikrein 8 (Table VIII). These two enzymes possess different enzymatic specificities (hK2: trypsin-like, hK3: chymotrypsin-like) but are naturally inhibited by ACT. While ACT is considered to be the natural hK3 inhibitor in blood circulation, its inhibition of hK2 is weaker.

Figure 6:
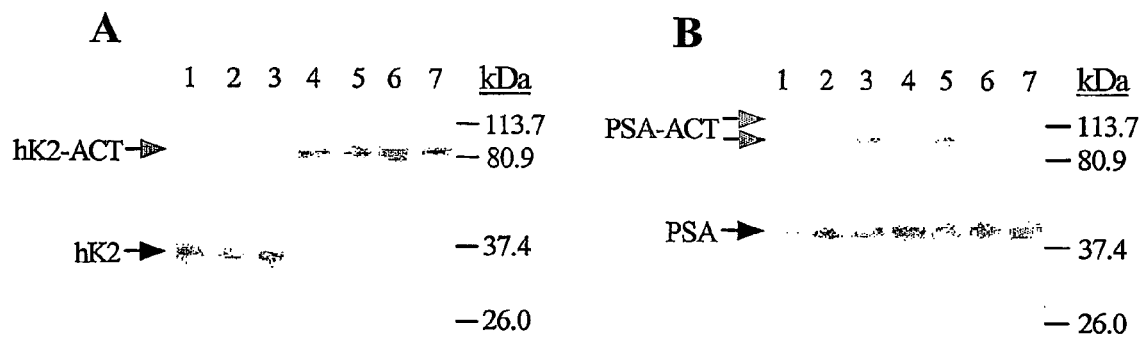
FIGS. 6 A and B show a Western Blot analysis of the inhibitory reaction between recombinant ACT and the human kallikreins hK2 (FIG. 6A) and PSA (FIG. 6B).

Analysis of the inhibitory reaction between rACTs and the human kallikreins were analysed by Western Blot as shown in FIG. 6. For each variants of ACT, 1 μg of inhibitor was incubated with 100 ng of either hK2 or hK3 during 1 hour at 37° C. under physiological conditions.

The results of the detection using the monoclonal antibody anti hK2 9D5 are shown in FIG. 6A.

Line 1: hK2 only, 2: commercial ACT+hK2, 3: wild type ACT+hK2, 4: MD820+hK2, 5: MDCI+hK2, 6: MD62+hK2, 7: MD61+hK2, FIG. 6 B shows the detection of hK3-ACT complex using antibody anti-His (tag present on recombinant ACT proteins).

Line 1: PSA, 2: PSA+ACT, 3: wild type ACT+PSA, 4: MD820+PSA, 5: MDCI+PSA, 6: MD62+PSA, 7: MD61+PSA.

The amino acid changes within the reactive loop using substrate sequences selected for hK2 specificity transformed ACT into an inhibitor highly specific for hK2 (MD820, MD61, MD62) without inhibiting hK3. These results confirm those previously shown in Table IV. Only MDCI, based on the reactive loop of the inhibitor of the Protein C (PCI) is able to inhibit both kallikreins tested (hK2 and hK3).

MD61 and MD62 are inhibitors with very high affinity for hK2 inhibiting all hK2 protein in less than 3 minutes (under the same conditions) compared to wild type or commercial α1-antichymotrypsin, which requires more than 12 hours of incubation to inhibit the same amount of hK2 (data not shown).

TABLE VIII

Inhibitory profile of $MD_{CI}$.

| Protease | Inhibition %[b] | SI | $k_a\ M^{-1}s^{-1}$ |
|---|---|---|---|
| Chymotrypsin | 98 | 1 | 86216 |
| Plasma Kallikrein | 100 | 4.6 | 25900 |
| Trypsin | 100 | 1 | 1126025 |
| Urokinase | 0 | — | — |
| Elastase | 0 | — | — |
| Thrombin | 0 | — | — |
| hK14 | 100 | 3.2 | 287000 |
| Human Kallikrein 8 | ~25 | ~180 | |

Example 3

Inhibition of Tumor Growth by MD Inhibitors 3.1 Inhibition of Tumor Growth by MD62 and MD 67 Inhibitors The androgen-independent human prostate adenocarcinoma cell line DU-145 was obtained from American Type Culture Collection. Retroviral technology was used to obtain DU145 cell transfected with hK2 gene (DU145/hK2).

Exponentially growing DU145/hK2 cells were collected and resuspended at a concentration of $7.5 \times 10^7$ cells/ml in DMEM (Invitrogen) containing 1 or 10 μg of inhibitors. This cell suspension was mixed with matrigel (BD Biosciences) at a 1:2 ratio and injected subcutaneously ($3 \times 10^6$ cells/40 μl) into the right and left flank of 8 week old male athymic Swiss nude mice (two mice/group). Each mouse was inoculated at two sites.

At days 6, 12 and 18 following tumor inoculation, 50 or 10 g of MD62, MD67 or 100 μg or 10 μg of ACT-WT were injected subcutaneously. At days 24, 30, 33, 36, 39 and 41 following tumor inoculation, 25 or 5 μg of inhibitors (MD62 and MD67) or 50 μg or 5 μg of ACT-WT were injected subcutaneously.

Figure 10:
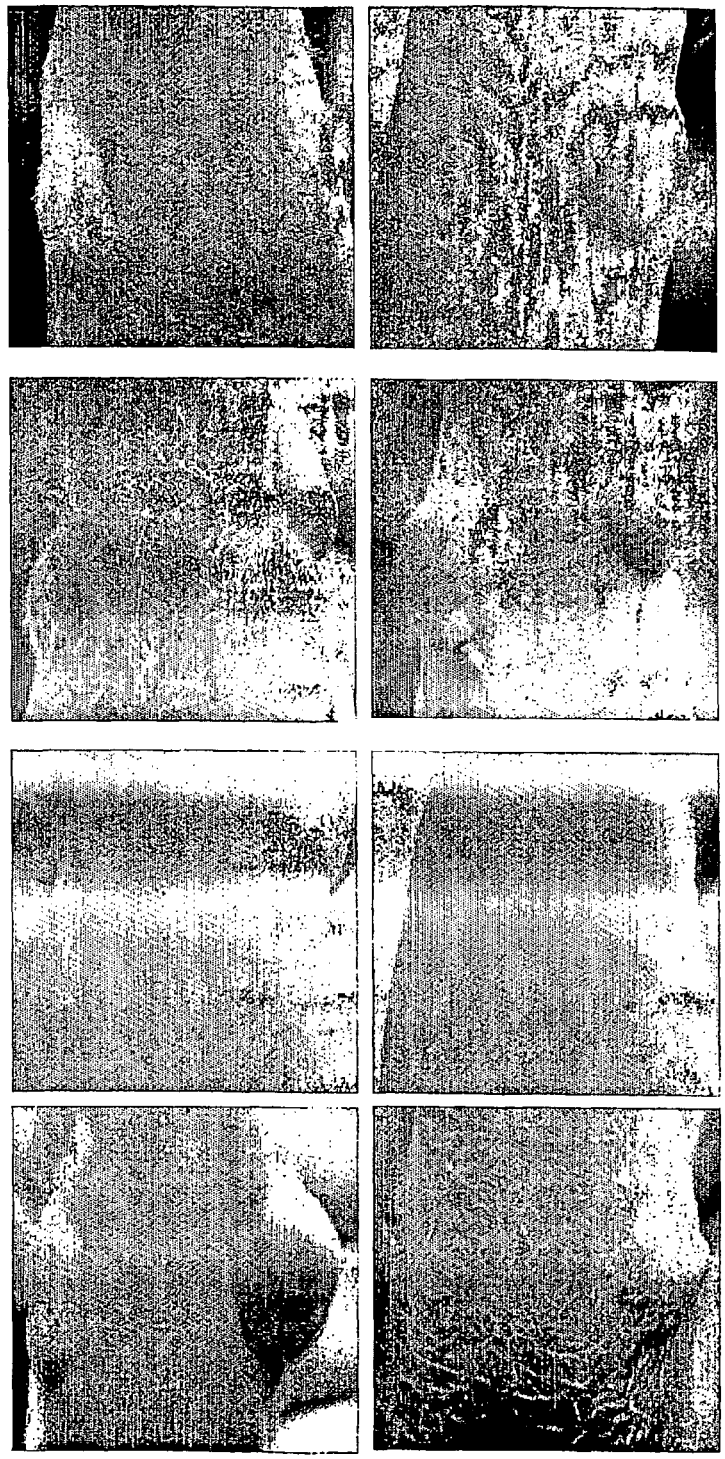
FIG. 10A shows the Inhibition of tumor growth by MD 62. Prostate cancer cells DU-145 ($3\times10^6$ cells), transfected with human kallikrein 2, were implanted in nude mice and then treated with MD 62 (5 or 25 µg/injection).
FIG. 10B shows the inhibition of tumor growth by MD 67. Prostate cancer cells DU-145 ($3\times10^6$ cells), transfected with human kallikrein 2, were implanted in nude mice and then treated with MD 67 (5 or 25 µg/injection).

FIG. 10A shows the Inhibition of tumor growth by MD 62. Prostate cancer cells DU-145 ($3 \times 10^6$ cells), transfected with human kallikrein 2, were implanted in nude mice and then treated with MD 62 (5 or 25 μg/injection).

FIG. 10B shows the inhibition of tumor growth by MD 67. Prostate cancer cells DU-145 ($3 \times 10^6$ cells), transfected with human kallikrein 2, were implanted in nude mice and then treated with MD 67 (5 or 25 μg/injection).

3.2 Inhibition of Tumor Growth by MDCI Inhibitor.

The androgen-independent human prostate adenocarcinoma cell line DU-145 was obtained from American Type Culture Collection. Retroviral technology was used to obtain DU145 cell transfected with hK2 gene (DU145/hK2).

Exponentially growing DU145/hK2 cells were collected and resuspended at a concentration of $7.5 \times 10^7$ cells/ml in DMEM (Invitrogen) containing 1 or 10 ug of inhibitors. This cell suspension was mixed with matrigel (BD Biosciences) at a 1:2 ratio and injected subcutaneously ($3 \times 10^6$ cells/40 μl) into the right and left flank of 8 week old male athymic Swiss nude mice (two mice/group). Each mouse was inoculated at two sites.

At days 6, 12 and 18 following tumor inoculation, 100 μg or 10 μg of MDCI or ACT-WT were injected subcutaneously. At days 24, 30, 33, 36, 39 and 41 following tumor inoculation, 50 μg or 5 μg of MDCI or ACT-WT were injected subcutaneously.

FIG. 11 shows the inhibition of tumor growth by MD CI. Prostate cancer cells DU-145 ($3 \times 10^6$ cells), transfected with human kallikrein 2, were implanted in nude mice and then treated with MD CI (5 or 50 ug/injection).

The invention claimed is:

1. A recombinant inhibitor protein, or an inhibiting fragment thereof, which inhibits a kallikrein, comprising an α-1 antichymotrypsin (ACT) serpin sequence with a modified Reactive Serpin Loop (RSL) wherein the modified RSL comprises the amino acid sequence set forth in SEQ ID NO: 16, SEQ ID NO: 17, SEQ ID NO: 18, SEQ ID NO: 19, SEQ ID NO: 20, SEQ ID NO: 21 or SEQ ID NO: 22.

2. The recombinant inhibitor protein, or inhibiting fragment thereof, which inhibits a kallikrein, of claim 1, wherein the kallikrein is hK2 kallikrein.

3. A pharmaceutical composition comprising the recombinant inhibitor protein, or inhibiting fragment thereof, of claim 1, and a pharmaceutically acceptable carrier.

4. A diagnostic kit for the detection of a kallikrein in a specimen comprising the recombinant inhibitor protein, or inhibiting fragment thereof, of claim 1.

5. A method for producing the recombinant inhibitor protein, or inhibiting fragment thereof, of claim 1, comprising a) selecting a polynucleotidic sequence encoding the modified Reactive Serpin Loop (RSL) which inhibits the Kallikrein by phage displayed library screening;

b) introducing the polynucleotidic sequence into a sequence encoding the α-1 antichymotrypsin (ACT) serpin, so as to obtain the recombinant inhibitor protein;

c) allowing expression of the recombinant inhibitor protein in a cell expression system under suitable conditions; and d) recovering the recombinant inhibitor protein.

6. The method of claim 5, wherein the suitable conditions comprise culturing the cell expression system at a temperature between 10-40° C. during 10-30 hours.

7. The method of claim 6, wherein the suitable conditions comprise a temperature of 16° C. during 16 hours.

8. The method of claim 5, wherein step d) is achieved by separation after extraction of the recombinant inhibitor protein, or inhibiting fragment thereof, from the cell expression system.

9. The method of claim 8, wherein the separation of the recombinant inhibitor protein, or inhibiting fragment thereof, is achieved by affinity chromatography.

10. The method of claim 5, wherein the cell expression system is a bacterial cell.

11. The method of claim 5, wherein the fragment is at least 40% of the length of the native ACT amino acid sequence.

12. The method of claim 5, wherein the fragment is at least 70% of the length of the native ACT amino acid sequence.

13. The method of claim 5, wherein the fragment is at least 80% of the length of the native ACT amino acid sequence.

14. The method of claim 5, wherein the fragment is at least 90% of the length of the native ACT amino acid sequence.

* * * * *

SEQUENCE LISTING

```
<160> NUMBER OF SEQ ID NOS: 130

<210> SEQ ID NO 1
<211> LENGTH: 1239
<212> TYPE: DNA
<213> ORGANISM: Artificial sequence
<220> FEATURE:
<223> OTHER INFORMATION: DNA Sequence ACT variants : MD 820

<400> SEQUENCE: 1
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct tctccccact gagcatctcc accgccttgg ccttcctgtc tctggggcc     240 cataatacca ccctgacaga gattctcaaa ggcctcaagt tcaacctcac ggagacttct     300
```

```
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gaccccaag  atactcatca gtcaaggttc    660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac tataacctga cgacatact  tctccagctg    960 ggcattgagg aagccttcac cagcaaggct gacctgtcag ggatcacagg gccaggaac    1020 ctagcagtct cccaggtggt ccataaggct gtgcttgatg tatttgagga gggcacagaa    1080
gcatctgctg ccaccgcggt caaaatcacc ctccgttctc gagcagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 2
<211> LENGTH: 412
<212> TYPE: PRT
<213> ORGANISM: Artificial sequence
<220> FEATURE:
<223> OTHER INFORMATION: Protein Sequence ACT variants : MD 820

<400> SEQUENCE: 2

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190
```

```
Met Met Val Leu Val Asn Tyr Ile Phe Phe Lys Ala Lys Trp Glu Met
            195                 200                 205
Pro Phe Asp Pro Gln Asp Thr His Gln Ser Arg Phe Tyr Leu Ser Lys
    210                 215                 220
Lys Lys Trp Val Met Val Pro Met Met Ser Leu His His Leu Thr Ile
225                 230                 235                 240
Pro Tyr Phe Arg Asp Glu Leu Ser Cys Thr Val Val Glu Leu Lys
                245                 250                 255
Tyr Thr Gly Asn Ala Ser Ala Leu Phe Ile Leu Pro Asp Gln Asp Lys
                260                 265                 270
Met Glu Glu Val Glu Ala Met Leu Leu Pro Gly Thr Leu Lys Arg Trp
            275                 280                 285
Arg Asp Ser Leu Glu Phe Arg Glu Ile Gly Glu Leu Tyr Leu Pro Lys
    290                 295                 300
Phe Ser Ile Ser Arg Asp Tyr Asn Leu Asn Asp Ile Leu Leu Gln Leu
305                 310                 315                 320
Gly Ile Glu Glu Ala Phe Thr Ser Lys Ala Asp Leu Ser Gly Ile Thr
                325                 330                 335
Gly Ala Arg Asn Leu Ala Val Ser Gln Val Val His Lys Ala Val Leu
                340                 345                 350
Asp Val Phe Glu Glu Gly Thr Glu Ala Ser Ala Ala Thr Ala Val Lys
            355                 360                 365
Ile Thr Leu Arg Ser Arg Ala Val Glu Thr Arg Thr Ile Val Arg Phe
    370                 375                 380
Asn Arg Pro Phe Leu Met Ile Ile Val Pro Thr Asp Thr Gln Asn Ile
385                 390                 395                 400
Phe Phe Met Ser Lys Val Thr Asn Pro Lys Gln Ala
                405                 410

<210> SEQ ID NO 3
<211> LENGTH: 1239
<212> TYPE: DNA
<213> ORGANISM: Artificial sequence
<220> FEATURE:
<223> OTHER INFORMATION: DNA Sequence ACT variant : MD 62

<400> SEQUENCE: 3
atgagaggat cccatcacca tcaccatcac tctagacacc ctaacagccc acttgacgag     60
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct tctccccact gagcatctcc accgccttgg ccttcctgtc tctgggggcc    240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gacccccaag atactcatca gtcaaggttc    660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
```

```
ctcccagaga ccctgaagcg gtggagagac tctctggagt tcagagagat aggtgagctc    900
tacctgccaa agttttccat ctcgagggac tataacctga acgacatact tctccagctg    960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcacc aggaggtcta tcgatgtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                          1239
```

<210> SEQ ID NO 4  
<211> LENGTH: 412  
<212> TYPE: PRT  
<213> ORGANISM: Artificial sequence  
<220> FEATURE:  
<223> OTHER INFORMATION: Protein Sequence ACT variant : MD 62

<400> SEQUENCE: 4

```
Met Arg Gly Ser His His His His His Ser His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285
```

```
Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
            325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
            355                 360                 365

Ile Thr Arg Arg Ser Ile Asp Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 5
<211> LENGTH: 1239
<212> TYPE: DNA
<213> ORGANISM: Artificial sequence
<220> FEATURE:
<223> OTHER INFORMATION: DNA Sequence ACT variant : MD 83

<400> SEQUENCE: 5
atgagaggat cccatcacca tcaccatcac tctagacacc ctaacagccc acttgacgag      60
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct ctctccccact gagcatctcc accgccttgg ccttcctgtc tctgggggcc    240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gacccccaag atactcatca gtcaaggttc    660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa gtttttccat tcgagggac tataacctga cgacatact tctccagctg     960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcagg gggagatctg agttagtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                          1239

<210> SEQ ID NO 6
<211> LENGTH: 412
```

```
<212> TYPE: PRT
<213> ORGANISM: Artificial sequence
<220> FEATURE:
<223> OTHER INFORMATION: Protein Sequence ACT variant : MD 83

<400> SEQUENCE: 6

Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Arg Gly Arg Ser Glu Leu Val Glu Thr Arg Thr Ile Val Arg Phe
370                 375                 380
```

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
            405                 410

<210> SEQ ID NO 7
<211> LENGTH: 1239
<212> TYPE: DNA
<213> ORGANISM: Artificial sequence
<220> FEATURE:
<223> OTHER INFORMATION: DNA Sequence ACT variant : MD 67

<400> SEQUENCE: 7
atgagaggat cccatcacca tcaccatcac tctagacacc taacagccc acttgacgag      60 gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct ctcccccact gagcatctcc accgccttgg ccttcctgtc tctgggggcc    240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag caactcag tctgctggac      420 aggttcacgg aggatgccaa gaggctgtat ggctccgagg cctttgccac tgactttcag    480
gactcagctg cagctaagaa gctcatcaac gactacgtga agaatggaac taggggaaa     540 atcacagatc tgatcaagga ccttgactcg cagacaatga tggtcctggt gaattacatc    600
ttctttaaag ccaaatggga gatgcccttt gaccccaag atactcatca gtcaaggttc      660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa gtttttccat ctcgagggac tataacctga cgacatact ctccagctg      960 ggcattgagg aagccttcac cagcaaggct gacctgtcag ggatcacagg gccaggaac    1020 ctagcagtct cccaggtggt ccataaggct gtgcttgatg tatttgagga gggcacagaa    1080
gcatctgctg ccaccgcggt caaaatcaag cttagaacaa cattagtgga gacgcgtacc    1140
attgtgcgtt caacaggcc cttcctgatg atcattgtcc ctacagacac ccagaacatc    1200
ttcttcatga gcaaagtcac caatcccaag caagcctaa                           1239

<210> SEQ ID NO 8
<211> LENGTH: 412
<212> TYPE: PRT
<213> ORGANISM: Artificial sequence
<220> FEATURE:
<223> OTHER INFORMATION: Protein Sequence ACT variant: MD 67

<400> SEQUENCE: 8

Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
            85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
            115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
            195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
            275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
            325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
            355                 360                 365

Ile Lys Leu Arg Thr Thr Leu Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 9
<211> LENGTH: 1239
<212> TYPE: DNA
<213> ORGANISM: Artificial sequence
<220> FEATURE:
<223> OTHER INFORMATION: DNA Sequence ACT variant : MD 61

<400> SEQUENCE: 9
atgagaggat cccatcacca tcaccatcac tctagacacc ctaacagccc acttgacgag    60

```
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct tctccccact gagcatctcc accgccttgg ccttcctgtc tctgggggcc    240
cataatacca ccctgacaga gattctcaaa ggcctcaagt caacctcac ggagacttct     300 gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gaccccaag atactcatca gtcaaggttc      660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatga aggaagtgga agccatgctg    840
ctcccagaga ccctgaagcg gtggagagac tctctggagt tcagagagat aggtgagctc    900
tacctgccaa agttttccat ctcgagggac tataacctga cgacatact ctctccagctg     960 ggcattgagg aagccttcac cagcaaggct gacctgtcag ggatcacagg gccaggaac    1020 ctagcagtct cccaggtggt ccataaggct gtgcttgatg tatttgagga gggcacagaa   1080
gcatctgctg ccaccgcggt caaaatcatg acaagatcta acgcagtgga gacgcgtacc   1140
attgtgcgtt tcaacaggcc cttcctgatg atcattgtcc ctacagacac ccagaacatc    1200
ttcttcatga gcaaagtcac caatcccaag caagcctaa                          1239
```

<210> SEQ ID NO 10
<211> LENGTH: 412
<212> TYPE: PRT
<213> ORGANISM: Artificial sequence
<220> FEATURE:
<223> OTHER INFORMATION: Protein Sequence ACT variant : MD 61

<400> SEQUENCE: 10

```
Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160
```

```
Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Met Thr Arg Ser Asn Ala Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 11
<211> LENGTH: 1239
<212> TYPE: DNA
<213> ORGANISM: Artificial sequence
<220> FEATURE:
<223> OTHER INFORMATION: DNA Sequence ACT variants : MD 518

<400> SEQUENCE: 11
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct ctccccact gagcatctcc accgccttgg ccttcctgtc tctgggggcc      240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggaaa      540 atcacagatc tgatcaagga ccttgactcg cagacaatga tggtcctggt gaattacatc     600
```

```
ttctttaaag ccaaatggga gatgcccttt gaccccaag atactcatca gtcaaggttc    660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgaggac tataacctga cgacatact tctccagctg    960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcacc gagcgtgtct cgcccgtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                          1239
```

<210> SEQ ID NO 12
<211> LENGTH: 412
<212> TYPE: PRT
<213> ORGANISM: Artificial sequence
<220> FEATURE:
<223> OTHER INFORMATION: Protein Sequence ACT variants: MD 518

<400> SEQUENCE: 12

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255
```

```
Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Thr Ala Val Lys
        355                 360                 365

Ile Thr Glu Arg Val Ser Pro Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 13
<211> LENGTH: 1239
<212> TYPE: DNA
<213> ORGANISM: Artificial sequence
<220> FEATURE:
<223> OTHER INFORMATION: DNA Sequence ACT variants : MD CI

<400> SEQUENCE: 13
atgagaggat cccatcacca tcaccatcac tctagacacc taacagccc acttgacgag        60 gagaatctga cccaggagaa ccaagaccga gggacacacg tggacctcgg attagcctcc      120
gccaacgtgg acttcgcttt cagcctgtac aagcagttag tcctgaaggc ccctgataag      180
aatgtcatct ctctcccact gagcatctcc accgccttgg ccttcctgtc tctgggggcc      240
cataatacca ccctgacaga gattctcaaa ggcctcaagt tcaacctcac ggagacttct      300
gaggcagaaa ttcaccagag cttccagcac ctcctgcgca ccctcaatca gtccagcgat      360
gagctgcagc tgagtatggg aaatgccatg tttgtcaaag agcaactcag tctgctggac      420
aggttcacgg aggatgccaa gaggctgtat ggctccgagg cctttgccac tgactttcag      480
gactcagctg cagctaagaa gctcatcaac gactacgtga agaatggaac tagggggaaa      540
atcacagatc tgatcaagga ccttgactcg cagacaatga tggtcctggt gaattacatc      600
ttctttaaag ccaaatggga gatgccctt gacccccaag atactcatca gtcaaggttc       660
tacttgagca agaaaaagtg ggtaatggtg cccatgatga gtttgcatca cctgactata      720
ccttacttcc gggacgagga gctgtcctgc accgtggtgg agctgaagta cacaggcaat      780
gccagcgcac tcttcatcct ccctgatcaa gacaagatgg aggaagtgga agccatgctg      840
ctcccagaga ccctgaagcg gtggagagac tctctggagt tcagagagat aggtgagctc      900
tacctgccaa agtttttcca tctcgaggga cataaaccga acgacatact ctctccagctg     960 ggcattgagg aagccttcac cagcaaggct gacctgtcag ggatcacagg ggccaggaac     1020
ctagcagtct cccaggtggt ccataaggct gtgcttgatg tatttgagga gggcacagaa     1080
gcatctgctg ccaccgcggt caaaatcacc tttagatctg cattagtgga gacgcgtacc     1140
```

```
attgtgcgtt tcaacaggcc cttcctgatg atcattgtcc ctacagacac ccagaacatc    1200
ttcttcatga gcaaagtcac caatcccaag caagcctaa                          1239
```

<210> SEQ ID NO 14
<211> LENGTH: 412
<212> TYPE: PRT
<213> ORGANISM: Artificial sequence
<220> FEATURE:
<223> OTHER INFORMATION: Protein Sequence ACT variants: MD CI

<400> SEQUENCE: 14

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350
```

```
Asp Val Phe Glu Glu Gly Thr Glu Ala Ser Ala Ala Thr Ala Val Lys
        355                 360                 365

Ile Thr Phe Arg Ser Ala Leu Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 15
<211> LENGTH: 11
<212> TYPE: PRT
<213> ORGANISM: Artificial sequence
<220> FEATURE:
<223> OTHER INFORMATION: RSL of ACT wild type

<400> SEQUENCE: 15

Val Lys Ile Thr Leu Leu Ser Ala Leu Val Glu
1               5                   10

<210> SEQ ID NO 16
<211> LENGTH: 11
<212> TYPE: PRT
<213> ORGANISM: Artificial sequence
<220> FEATURE:
<223> OTHER INFORMATION: RSL of MD820

<400> SEQUENCE: 16

Val Lys Ile Thr Leu Arg Ser Arg Ala Val Glu
1               5                   10

<210> SEQ ID NO 17
<211> LENGTH: 11
<212> TYPE: PRT
<213> ORGANISM: Artificial sequence
<220> FEATURE:
<223> OTHER INFORMATION: RSL of ACT 62

<400> SEQUENCE: 17

Val Lys Ile Thr Arg Arg Ser Ile Asp Val Glu
1               5                   10

<210> SEQ ID NO 18
<211> LENGTH: 11
<212> TYPE: PRT
<213> ORGANISM: Artificial sequence
<220> FEATURE:
<223> OTHER INFORMATION: RSL of MD83

<400> SEQUENCE: 18

Val Lys Ile Arg Gly Arg Ser Glu Leu Val Glu
1               5                   10

<210> SEQ ID NO 19
<211> LENGTH: 11
<212> TYPE: PRT
<213> ORGANISM: Artificial sequence
<220> FEATURE:
<223> OTHER INFORMATION: RSL of MD 67

<400> SEQUENCE: 19

Val Lys Ile Lys Leu Arg Thr Thr Leu Val Glu
1               5                   10
```

```
<210> SEQ ID NO 20
<211> LENGTH: 11
<212> TYPE: PRT
<213> ORGANISM: Artificial sequence
<220> FEATURE:
<223> OTHER INFORMATION: RSL of MD 61

<400> SEQUENCE: 20

Val Lys Ile Met Thr Arg Ser Asn Ala Val Glu
1               5                   10

<210> SEQ ID NO 21
<211> LENGTH: 11
<212> TYPE: PRT
<213> ORGANISM: Artificial sequence
<220> FEATURE:
<223> OTHER INFORMATION: RSL of MD 518

<400> SEQUENCE: 21

Val Lys Ile Thr Glu Arg Val Ser Pro Val Glu
1               5                   10

<210> SEQ ID NO 22
<211> LENGTH: 11
<212> TYPE: PRT
<213> ORGANISM: Artificial sequence
<220> FEATURE:
<223> OTHER INFORMATION: RSL of MD CI

<400> SEQUENCE: 22

Val Lys Ile Thr Phe Arg Ser Ala Leu Val Glu
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide

<400> SEQUENCE: 23

Ser Ser Arg Thr Glu
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Lys Thr Arg Ser Asn
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25

Ile Ser Pro Arg Ser
1               5

<210> SEQ ID NO 26
```

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

Gly Val Phe Arg Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide

<400> SEQUENCE: 27

Gly Thr Val Arg Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Glu Thr Lys Arg Ser
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide

<400> SEQUENCE: 29

Leu Gly Arg Ser Leu
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide

<400> SEQUENCE: 30

Arg Gly Arg Ser Glu
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Arg Arg Ser Ile Asp
1               5

<210> SEQ ID NO 32
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 32

Val Leu Arg Ser Pro
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

Pro Phe Arg Ser Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

Arg Ser Gly Ser Val
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide

<400> SEQUENCE: 35

Ala Arg Ala Arg Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide

<400> SEQUENCE: 36

Ser Asp Arg Thr Ala
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Lys Leu Arg Thr Thr
1               5

<210> SEQ ID NO 38
<211> LENGTH: 5
<212> TYPE: PRT
```

```
<213> ORGANISM: Artificial Sequence
<220> FEATURE:
<223> OTHER INFORMATION: Synthetic peptide

<400> SEQUENCE: 38

Arg Ala Ala Met Met
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39

Thr Arg Ala Pro Met
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Asp Val Arg Ala Ala
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Pro Gly Arg Ala Pro
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide

<400> SEQUENCE: 42

Val Arg Ser Arg Ala
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide

<400> SEQUENCE: 43

Ala Arg Ala Ser Glu
1               5

<210> SEQ ID NO 44
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 44

Thr Leu Gln Arg Val
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

Arg Leu Glu Arg Val
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Glu Arg Val Ser Pro
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide

<400> SEQUENCE: 47

Ser Ser Phe Arg Val
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide

<400> SEQUENCE: 48

Arg Val Gly Pro Tyr
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide

<400> SEQUENCE: 49

Pro Ser Ala Arg Met
1               5

<210> SEQ ID NO 50
<211> LENGTH: 5
<212> TYPE: PRT
<213> ORGANISM: Artificial Sequence
<220> FEATURE:
```

```
<223> OTHER INFORMATION: Synthetic peptide

<400> SEQUENCE: 50

Arg Gly Arg Met Ala
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic peptide

<400> SEQUENCE: 51

Thr Val Arg Met Pro
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide

<400> SEQUENCE: 52

Leu Arg Met Pro Thr
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic peptide

<400> SEQUENCE: 53

His Arg Met Ser Ser
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic peptide

<400> SEQUENCE: 54

Arg Pro Gln Ser Leu
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic peptide

<400> SEQUENCE: 55

Val Arg Pro Leu Glu
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic peptide
```

<400> SEQUENCE: 56

Ser Gly Arg Leu Ala
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic peptide

<400> SEQUENCE: 57

Gly Thr Leu Arg Phe
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic peptide

<400> SEQUENCE: 58

Gln Trp Arg Asn Ser
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic peptide

<400> SEQUENCE: 59

Arg Asn Asp Lys Leu
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic peptide

<400> SEQUENCE: 60

Met Arg Asn Leu Ala
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic peptide

<400> SEQUENCE: 61

Thr Arg Asp Ser Arg
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic peptide

```
<400> SEQUENCE: 62

Thr Gly Ser Arg Asp
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic peptide

<400> SEQUENCE: 63

Ile Met Ser Arg Gln
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Glu Gln His Arg Gln Met Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic peptide

<400> SEQUENCE: 65

Leu Thr Thr Ser Lys
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic peptide

<400> SEQUENCE: 66

Pro Phe Arg Lys Ile
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic peptide

<400> SEQUENCE: 67

Met Thr Arg Ser Asn
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic peptide

<400> SEQUENCE: 68
```

Leu Arg Ser Arg Ala
1               5

<210> SEQ ID NO 69
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 69
gtcaaaatca ccctcctttc tgcattagtg gag                33

<210> SEQ ID NO 70
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 70
gtcaaaatca ccctccgttc tcgagcagtg gag                33

<210> SEQ ID NO 71
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 71
gtcaaaatca ccaggaggtc tatcgatgtg gag                33

<210> SEQ ID NO 72
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 72
gtcaaaatca gggggagatc tgagttagtg gag                33

<210> SEQ ID NO 73
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 73
gtcaaaatca agcttagaac aacattagtg gag                33

<210> SEQ ID NO 74
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 74
gtcaaaatca tgacaagatc taacgcagtg gag                33

<210> SEQ ID NO 75
<211> LENGTH: 33

```
<212> TYPE: DNA
<213> ORGANISM: Artificial Sequence
<220> FEATURE:
<223> OTHER INFORMATION: Synthetic oligonucleotide

<400> SEQUENCE: 75
gtcaaaatca ccgagcgtgt ctcgcccgtg gag                                    33

<210> SEQ ID NO 76
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 76
gtcaaaatca cctttagatc tgcattagtg gag                                    33

<210> SEQ ID NO 77
<211> LENGTH: 20
<212> TYPE: PRT
<213> ORGANISM: Homo sapiens

<400> SEQUENCE: 77

Gly Thr Glu Ala Ala Gly Ala Met Phe Leu Glu Ala Ile Pro Met Ser
1               5                   10                  15

Ile Pro Pro Glu
            20

<210> SEQ ID NO 78
<211> LENGTH: 20
<212> TYPE: PRT
<213> ORGANISM: Homo sapiens

<400> SEQUENCE: 78

Gly Thr Glu Ala Thr Gly Ala Pro His Leu Glu Glu Lys Ala Trp Ser
1               5                   10                  15

Lys Tyr Gln Thr
            20

<210> SEQ ID NO 79
<211> LENGTH: 20
<212> TYPE: PRT
<213> ORGANISM: Homo sapiens

<400> SEQUENCE: 79

Gly Val Glu Ala Ala Ala Ala Thr Ser Ile Ala Met Ser Arg Met Ser
1               5                   10                  15

Leu Ser Ser Phe
            20

<210> SEQ ID NO 80
<211> LENGTH: 20
<212> TYPE: PRT
<213> ORGANISM: Homo sapiens

<400> SEQUENCE: 80

Gly Thr Glu Ala Ser Ala Ala Thr Ala Val Lys Ile Thr Leu Leu Ser
1               5                   10                  15

Ala Leu Val Glu
            20

<210> SEQ ID NO 81
```

-continued

```
<211> LENGTH: 20
<212> TYPE: PRT
<213> ORGANISM: Homo sapiens

<400> SEQUENCE: 81

Gly Ser Glu Ala Ala Ser Thr Ala Val Val Ile Ala Gly Arg Ser
1               5                   10                  15

Leu Asn Pro Asn
            20

<210> SEQ ID NO 82
<211> LENGTH: 20
<212> TYPE: PRT
<213> ORGANISM: Homo sapiens

<400> SEQUENCE: 82

Gly Thr Glu Ala Ala Ala Gly Ser Gly Ser Glu Ile Asp Ile Arg Ile
1               5                   10                  15

Arg Val Pro Ser
            20

<210> SEQ ID NO 83
<211> LENGTH: 20
<212> TYPE: PRT
<213> ORGANISM: Homo sapiens

<400> SEQUENCE: 83

Gly Asn Pro Phe Asp Gln Asp Ile Tyr Gly Arg Glu Glu Leu Arg Ser
1               5                   10                  15

Pro Lys Leu Phe
            20

<210> SEQ ID NO 84
<211> LENGTH: 20
<212> TYPE: PRT
<213> ORGANISM: Homo sapiens

<400> SEQUENCE: 84

Gly Thr Lys Ala Ser Ala Ala Thr Thr Ala Ile Leu Ile Ala Arg Ser
1               5                   10                  15

Ser Pro Pro Trp
            20

<210> SEQ ID NO 85
<211> LENGTH: 20
<212> TYPE: PRT
<213> ORGANISM: Homo sapiens

<400> SEQUENCE: 85

Gly Thr Gln Ala Thr Thr Val Thr Val Gly Phe Met Pro Leu Ser
1               5                   10                  15

Thr Gln Val Arg
            20

<210> SEQ ID NO 86
<211> LENGTH: 20
<212> TYPE: PRT
<213> ORGANISM: Homo sapiens

<400> SEQUENCE: 86

Gly Val Glu Ala Ala Ala Ser Ala Ile Ser Val Ala Arg Thr Leu
1               5                   10                  15
```

Leu Val Phe Glu
        20

<210> SEQ ID NO 87
<211> LENGTH: 20
<212> TYPE: PRT
<213> ORGANISM: Homo sapiens

<400> SEQUENCE: 87

Gly Thr Glu Ala Ala Ala Thr Ala Gly Ile Ala Thr Phe Cys Met
1               5                   10                  15

Leu Met Pro Glu
        20

<210> SEQ ID NO 88
<211> LENGTH: 20
<212> TYPE: PRT
<213> ORGANISM: Homo sapiens

<400> SEQUENCE: 88

Gly Thr Arg Ala Ala Ala Ala Thr Gly Thr Ile Phe Thr Phe Arg Ser
1               5                   10                  15

Ala Arg Leu Asn
        20

<210> SEQ ID NO 89
<211> LENGTH: 20
<212> TYPE: PRT
<213> ORGANISM: Homo sapiens

<400> SEQUENCE: 89

Gly Thr Glu Ala Ala Ala Ala Thr Thr Phe Ala Ile Lys Phe Phe Ser
1               5                   10                  15

Ala Gln Thr Asn
        20

<210> SEQ ID NO 90
<211> LENGTH: 20
<212> TYPE: PRT
<213> ORGANISM: Homo sapiens

<400> SEQUENCE: 90

Gly Gly Asp Ser Ile Glu Val Pro Gly Ala Arg Ile Leu Gln His Lys
1               5                   10                  15

Asp Glu Leu Asn
        20

<210> SEQ ID NO 91
<211> LENGTH: 20
<212> TYPE: PRT
<213> ORGANISM: Homo sapiens

<400> SEQUENCE: 91

Gly Ser Glu Ala Ala Ala Val Ser Gly Met Ile Ala Ile Ser Arg Met
1               5                   10                  15

Ala Val Leu Tyr
        20

<210> SEQ ID NO 92
<211> LENGTH: 20
<212> TYPE: PRT
<213> ORGANISM: Homo sapiens

```
<400> SEQUENCE: 92

Gly Thr Val Ala Ser Ser Thr Ala Val Ile Val Ser Ala Arg Met
1               5                   10                  15

Ala Pro Glu Glu
            20

<210> SEQ ID NO 93
<211> LENGTH: 20
<212> TYPE: PRT
<213> ORGANISM: Homo sapiens

<400> SEQUENCE: 93

Gly Thr Glu Ala Ala Gly Thr Gly Gly Val Met Thr Gly Arg Thr
1               5                   10                  15

Gly His Gly Gly
            20

<210> SEQ ID NO 94
<211> LENGTH: 20
<212> TYPE: PRT
<213> ORGANISM: Homo sapiens

<400> SEQUENCE: 94

Gly Ala Gly Thr Thr Pro Ser Pro Gly Leu Gln Pro Ala His Leu Thr
1               5                   10                  15

Phe Pro Leu Asp
            20

<210> SEQ ID NO 95
<211> LENGTH: 20
<212> TYPE: PRT
<213> ORGANISM: Homo sapiens

<400> SEQUENCE: 95

Gly Thr Glu Ala Ala Ala Ala Thr Ala Ala Ile Met Met Met Arg Cys
1               5                   10                  15

Ala Arg Phe Val
            20

<210> SEQ ID NO 96
<211> LENGTH: 20
<212> TYPE: PRT
<213> ORGANISM: Homo sapiens

<400> SEQUENCE: 96

Gly Thr Glu Ala Ala Ala Ala Thr Ala Val Val Arg Asn Ser Arg Cys
1               5                   10                  15

Ser Arg Met Glu
            20

<210> SEQ ID NO 97
<211> LENGTH: 20
<212> TYPE: PRT
<213> ORGANISM: Homo sapiens

<400> SEQUENCE: 97

Gly Thr Glu Ala Ala Ala Ala Ser Ser Cys Phe Val Val Ala Glu Cys
1               5                   10                  15

Cys Met Glu Ser
            20
```

```
<210> SEQ ID NO 98
<211> LENGTH: 20
<212> TYPE: PRT
<213> ORGANISM: Homo sapiens

<400> SEQUENCE: 98

Gly Ala Glu Ala Ala Ala Thr Ala Val Val Gly Phe Gly Ser Ser
1               5                   10                  15

Pro Ala Ser Thr
            20

<210> SEQ ID NO 99
<211> LENGTH: 20
<212> TYPE: PRT
<213> ORGANISM: Homo sapiens

<400> SEQUENCE: 99

Gly Val Glu Ala Ala Ala Thr Ala Val Val Val Glu Leu Ser
1               5                   10                  15

Ser Pro Ser Thr
            20

<210> SEQ ID NO 100
<211> LENGTH: 20
<212> TYPE: PRT
<213> ORGANISM: Homo sapiens

<400> SEQUENCE: 100

Gly Thr Glu Ala Ala Ala Val Pro Glu Val Glu Leu Ser Asp Gln Pro
1               5                   10                  15

Glu Asn Thr Phe
            20

<210> SEQ ID NO 101
<211> LENGTH: 20
<212> TYPE: PRT
<213> ORGANISM: Homo sapiens

<400> SEQUENCE: 101

Gly Thr Glu Ala Thr Ala Ala Thr Gly Ser Asn Ile Val Glu Lys Gln
1               5                   10                  15

Leu Pro Gln Ser
            20

<210> SEQ ID NO 102
<211> LENGTH: 20
<212> TYPE: PRT
<213> ORGANISM: Homo sapiens

<400> SEQUENCE: 102

Gly Ser Glu Ala Ala Thr Ser Thr Gly Ile His Ile Pro Val Ile Met
1               5                   10                  15

Ser Leu Ala Gln
            20

<210> SEQ ID NO 103
<211> LENGTH: 4
<212> TYPE: PRT
<213> ORGANISM: Artificial Sequence
<220> FEATURE:
<223> OTHER INFORMATION: Synthetic peptide

<400> SEQUENCE: 103
```

Ala Ala Pro Phe
1

<210> SEQ ID NO 104
<211> LENGTH: 4
<212> TYPE: PRT
<213> ORGANISM: Artificial Sequence
<220> FEATURE:
<223> OTHER INFORMATION: Synthetic peptide

<400> SEQUENCE: 104

Ala Ala Pro Val
1

<210> SEQ ID NO 105
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 105
gtgattttga ccgcggtggc agcag                                         25

<210> SEQ ID NO 106
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 106
gcacaatggt acgcgtctcc actaatg                                       27

<210> SEQ ID NO 107
<211> LENGTH: 4
<212> TYPE: PRT
<213> ORGANISM: Artificial Sequence
<220> FEATURE:
<223> OTHER INFORMATION: Synthetic peptide

<400> SEQUENCE: 107

Gly Gly Gly Ser
1

<210> SEQ ID NO 108
<211> LENGTH: 70
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)

<223> OTHER INFORMATION: n is a, c, g, or t

<400> SEQUENCE: 108
tgagctagtc tagataggtg gcggtnnsnn snnsnnsnns gggtcgacgt cggtcatagc    60
agtcgctgca                                                          70

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
tgagctagtc tagataggtg                                               20

<210> SEQ ID NO 110
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 110
tgcagcgact gctatga                                                  17

<210> SEQ ID NO 111
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 111
taccgcggtc aaaatcaccc tccgttctcg agcagtggag acgcgtga                48

<210> SEQ ID NO 112
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 112
taccgcggtc aaaatcacca ggaggtctat cgatgtggag acgcgtga                48

<210> SEQ ID NO 113
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 113
taccgcggtc aaaatcaggg ggagatctga gttagtggag acgcgtga                48

<210> SEQ ID NO 114
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 114
taccgcggtc aaaatcaagc ttagaacaac attagtggag accgctga                48

<210> SEQ ID NO 115
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 115
taccgcggtc aaaatcatga caagatctaa cttagtggag acgcgtga         48

<210> SEQ ID NO 116
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 116
taccgcggtc aaaatcaccg agcgtgtctc gcccgtggag acgcgtga         48

<210> SEQ ID NO 117
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 117
taccgcggtc aaaatc         16

<210> SEQ ID NO 118
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 118
tcacgcgtgt ccac         14

<210> SEQ ID NO 119
<211> LENGTH: 12
<212> TYPE: PRT
<213> ORGANISM: Artificial Sequence
<220> FEATURE:
<223> OTHER INFORMATION: Synthetic peptide

<400> SEQUENCE: 119

Val Lys Ile Thr Leu Leu Ser Ala Leu Val Glu Thr
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Synthetic peptide

<400> SEQUENCE: 120

Val Lys Ile Thr Leu Arg Ser Arg Ala Val Glu Thr
1               5                   10

<210> SEQ ID NO 121
<211> LENGTH: 12
<212> TYPE: PRT

```
<213> ORGANISM: Artificial Sequence
<220> FEATURE:
<223> OTHER INFORMATION: Synthetic peptide

<400> SEQUENCE: 121

Val Lys Ile Thr Arg Arg Ser Ile Asp Val Glu Thr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic peptide

<400> SEQUENCE: 122

Val Lys Ile Arg Gly Arg Ser Glu Leu Val Glu Thr
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic peptide

<400> SEQUENCE: 123

Val Lys Ile Lys Leu Arg Thr Thr Leu Val Glu Thr
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic peptide

<400> SEQUENCE: 124

Val Lys Ile Met Thr Arg Ser Asn Ala Val Glu Thr
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic peptide

<400> SEQUENCE: 125

Val Lys Ile Thr Glu Arg Val Ser Pro Val Glu Thr
1               5                   10

<210> SEQ ID NO 126
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 126
gtcaaaatca ccctcctttc tgcattagtg gaggtc                                 36

<210> SEQ ID NO 127
<211> LENGTH: 12
<212> TYPE: PRT
<213> ORGANISM: Artificial Sequence
<220> FEATURE:
```

```
<223> OTHER INFORMATION: Synthetic peptide

<400> SEQUENCE: 127

Thr Ile Phe Thr Phe Arg Ser Ala Arg Leu Asn Ser
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic peptide

<400> SEQUENCE: 128

Val Lys Ile Thr Phe Arg Ser Ala Leu Val Glu Thr
1               5                   10

<210> SEQ ID NO 129
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 129
gtcaaaatca cctttagatc tgcattagtg gaggtc                               36

<210> SEQ ID NO 130
<211> LENGTH: 5
<212> TYPE: PRT
<213> ORGANISM: Artificial Sequence
<220> FEATURE:
<223> OTHER INFORMATION: Synthetic peptide

<400> SEQUENCE: 130

Thr Phe Arg Ser Ala
1               5
```